(12) United States Patent
Murakami

(10) Patent No.: US 11,851,684 B2
(45) Date of Patent: Dec. 26, 2023

(54) EXPRESSION CASSETTE

(71) Applicant: Spiber Inc., Yamagata (JP)

(72) Inventor: Masahiro Murakami, Tsuruoka (JP)

(73) Assignee: Spiber Inc., Yamagata (JP)

(*) Notice: Subject to any disclaimer, the term of this patent is extended or adjusted under 35 U.S.C. 154(b) by 443 days.

(21) Appl. No.: 16/649,804

(22) PCT Filed: Sep. 28, 2018

(86) PCT No.: PCT/JP2018/036259
§ 371 (c)(1),
(2) Date: Mar. 23, 2020

(87) PCT Pub. No.: WO2019/065968
PCT Pub. Date: Apr. 4, 2019

(65) Prior Publication Data
US 2020/0308552 A1    Oct. 1, 2020

(30) Foreign Application Priority Data

Sep. 29, 2017 (JP) ................................. 2017-191063

(51) Int. Cl.
*C12N 5/10* (2006.01)
*C12N 15/11* (2006.01)
*C12P 21/02* (2006.01)

(52) U.S. Cl.
CPC .............. *C12N 5/10* (2013.01); *C12N 15/111* (2013.01); *C12P 21/02* (2013.01)

(58) Field of Classification Search
CPC ...... C12N 5/10; C12N 15/111; C12N 15/635; C12N 15/67; C12P 21/02; C12Y 301/21001; C12Y 302/01017
See application file for complete search history.

(56) References Cited

U.S. PATENT DOCUMENTS

2007/0214520 A1* 9/2007 Scheibel .......... C07K 14/43518
                                                435/254.2
2010/0323426 A1* 12/2010 Bower ................. C12N 9/2437
                                                435/254.9
2017/0066804 A1* 3/2017 Nakase .................. C12N 15/70

FOREIGN PATENT DOCUMENTS

| JP | S63-287489 A | 11/1988 |
|---|---|---|
| JP | 2003-219895 A | 8/2003 |
| JP | 2006-511220 A | 4/2006 |
| JP | 2008-506409 A | 3/2008 |
| JP | 2010-528655 A | 8/2010 |
| JP | 2012-531889 A | 12/2012 |
| WO | 03/100065 A1 | 12/2003 |
| WO | 2004/058947 A2 | 7/2004 |
| WO | 2006/008163 A2 | 1/2006 |
| WO | 2008/153903 A2 | 12/2008 |
| WO | 2010/123450 A1 | 10/2010 |
| WO | 2015/178465 A1 | 11/2015 |
| WO | 2015/178466 A1 | 11/2015 |

OTHER PUBLICATIONS

PET System Manual. 1999. Novagen. p. 1-50 (Year: 1999).*
Yu H et al. 2000. Construction and Selection of the Novel Recombinant *Escherichia coli* Strain for Poly(beta-hydroxybutyrate) Production. vol. 89, No. 4, 307-311. (Year: 2000).*
International Search Report issued in corresponding International Patent Application No. PCT/2018/036259 dated Dec. 4, 2018.
International Preliminary Report on Patentability and Written Opinion issued in corresponding International Patent Application No. PCT/2018/036259 dated Apr. 9, 2020.
Humin Y. et al., "Construction and Selection of the Novel Recombinant *Escherichia coli* Strain for Poly(beta-Hydroxybutyrate) Production," Journal of Bioscience and Bioengineering, 89: 307-311 (2000).
Beuzon et al., "Repression of IS200 transposases synthesis by RNA secondary structures," Nucleic Acids Research, 27: 3690-3695 (1999).

* cited by examiner

*Primary Examiner* — Paul J Holland

(74) *Attorney, Agent, or Firm* — Morgan, Lewis & Bockius LLP

(57) ABSTRACT

Disclosed is an expression cassette comprising, in a 5' to 3' direction of a sense strand, a promoter, and a first nucleic acid, a terminator and a second nucleic acid operably linked to the promoter, wherein the first nucleic acid and the second nucleic acid each contain at least one gene.

16 Claims, 4 Drawing Sheets

Specification includes a Sequence Listing.

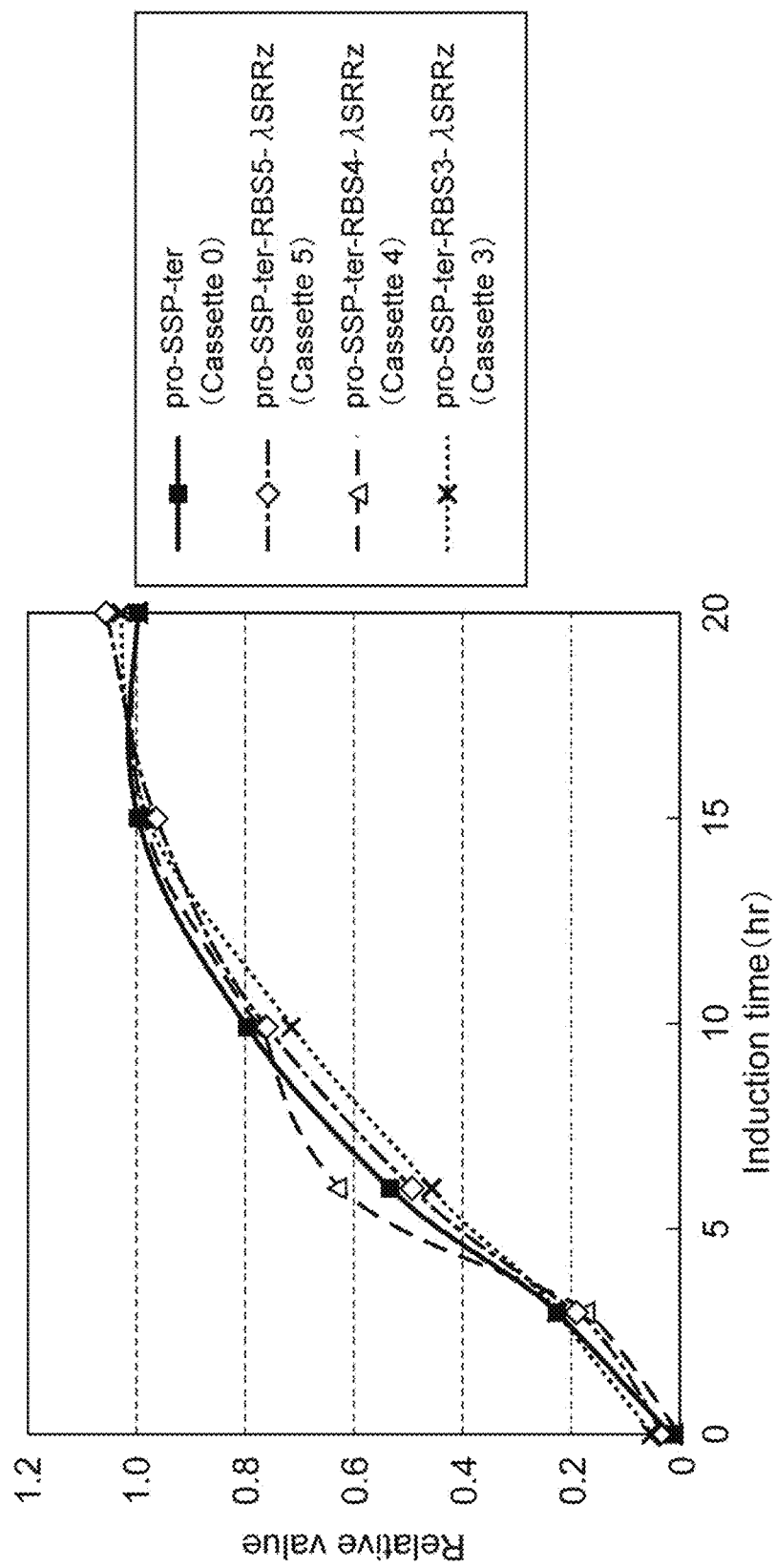

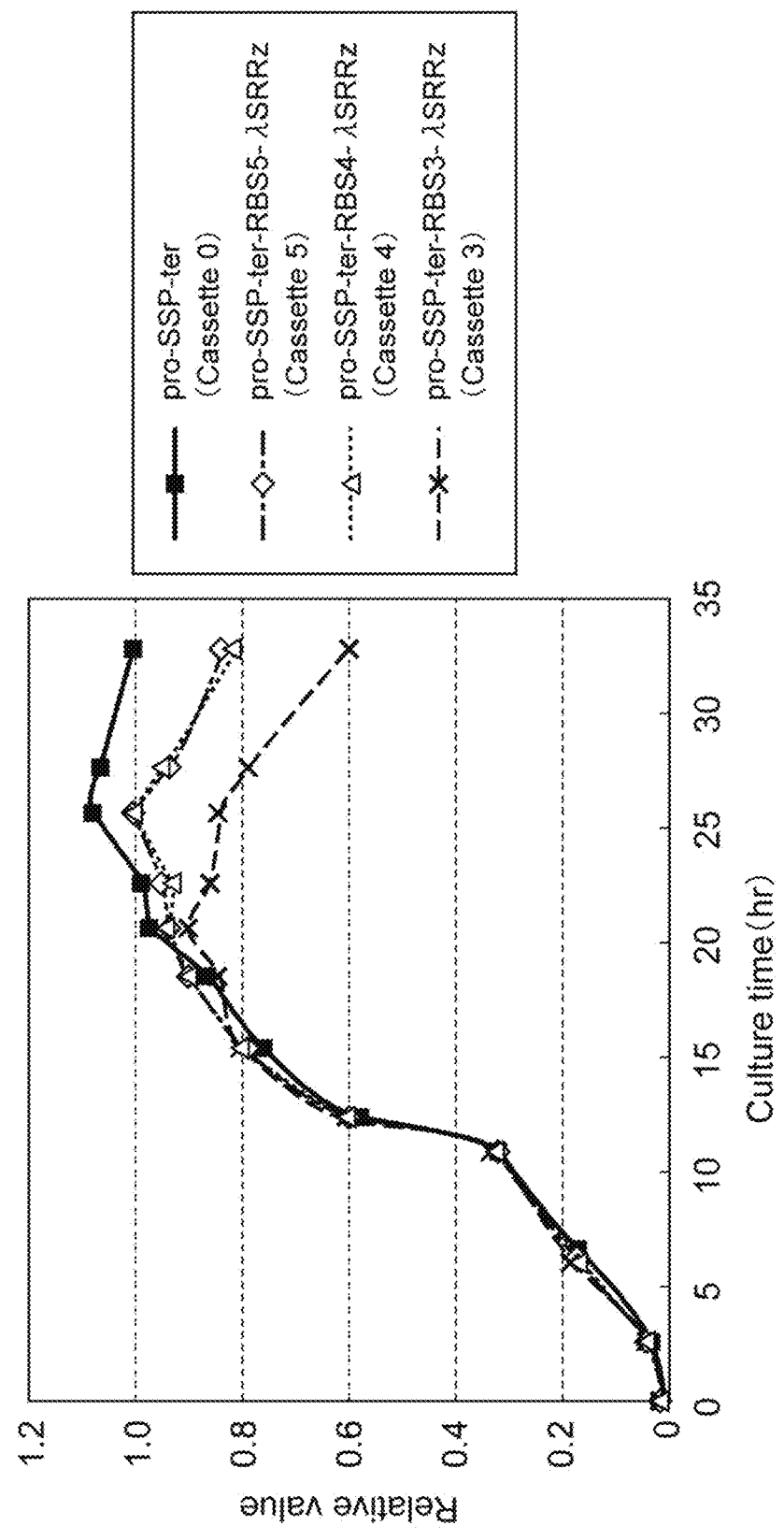

SEQUENCE LISTING

<160> NUMBER OF SEQ ID NOS: 15

<210> SEQ ID NO 1
<211> LENGTH: 282
<212> TYPE: PRT
<213> ORGANISM: Artificial Sequence
<220> FEATURE:

<223> OTHER INFORMATION: elastin short

<400> SEQUENCE: 1

Met His His His His His Ser Ser Gly Ser Ser Leu Gly Val Ser
1               5                   10                  15

Ala Gly Ala Val Val Pro Gln Pro Gly Ala Gly Val Lys Pro Gly Lys
            20                  25                  30

Val Pro Gly Val Gly Leu Pro Gly Val Tyr Pro Gly Gly Val Leu Pro
            35                  40                  45

Gly Ala Arg Phe Pro Gly Val Gly Val Leu Pro Gly Val Pro Thr Gly
        50                  55                  60

Ala Gly Val Lys Pro Lys Ala Pro Gly Val Gly Gly Ala Phe Ala Gly
65                  70                  75                  80

Ile Pro Gly Val Gly Pro Phe Gly Gly Pro Gln Pro Gly Val Pro Leu
                85                  90                  95

Gly Tyr Pro Ile Lys Ala Pro Lys Leu Pro Gly Gly Tyr Gly Leu Pro
            100                 105                 110

Tyr Thr Thr Gly Lys Leu Pro Tyr Gly Tyr Gly Pro Gly Gly Val Ala
            115                 120                 125

Gly Ala Ala Gly Lys Ala Gly Tyr Pro Thr Gly Thr Gly Val Gly Pro
        130                 135                 140

Gln Ala Ala Ala Ala Ala Ala Lys Ala Ala Ala Lys Phe Gly Ala
145                 150                 155                 160

Gly Ala Ala Gly Val Leu Pro Gly Val Gly Gly Ala Gly Val Pro Gly
                165                 170                 175

Val Pro Gly Ala Ile Pro Gly Ile Gly Gly Ile Ala Gly Val Gly Thr
            180                 185                 190

Pro Ala Ala Ala Ala Ala Ala Ala Ala Lys Ala Ala Lys Tyr
            195                 200                 205

Gly Ala Ala Ala Gly Leu Val Pro Gly Gly Pro Gly Phe Gly Pro Gly
        210                 215                 220

Val Val Gly Val Pro Gly Ala Gly Val Pro Gly Val Gly Val Pro Gly
225                 230                 235                 240

Ala Gly Ile Pro Val Val Pro Gly Ala Gly Ile Pro Gly Ala Ala Val
                245                 250                 255

Pro Gly Val Val Ser Pro Glu Ala Ala Ala Lys Ala Ala Ala Lys Ala
            260                 265                 270

Ala Lys Tyr Gly Ala Arg Pro Gly Val Gly
        275                 280

<210> SEQ ID NO 2
<211> LENGTH: 468
<212> TYPE: PRT
<213> ORGANISM: Artificial Sequence
<220> FEATURE:
<223> OTHER INFORMATION: type I keratin 26

<400> SEQUENCE: 2

Met Ser Phe Arg Leu Ser Gly Val Ser Arg Arg Leu Cys Ser Gln Ala
1               5                   10                  15

Gly Thr Gly Arg Leu Thr Gly Gly Arg Thr Gly Phe Arg Ala Gly Asn
            20                  25                  30

Val Cys Ser Gly Leu Gly Ala Gly Ser Ser Phe Ser Gly Pro Leu Gly
            35                  40                  45

Ser Val Ser Ser Lys Gly Ser Phe Ser His Gly Gly Gly Gly Leu Gly
        50                  55                  60

```
Ser Gly Val Cys Thr Gly Phe Leu Glu Asn Glu His Gly Leu Leu Pro
 65                  70                  75                  80

Gly Asn Glu Lys Val Thr Leu Gln Asn Leu Asn Asp Arg Leu Ala Ser
                 85                  90                  95

Tyr Leu Asp His Val Cys Thr Leu Glu Glu Ala Asn Ala Asp Leu Glu
            100                 105                 110

Gln Lys Ile Lys Gly Trp Tyr Glu Lys Tyr Gly Pro Gly Ser Gly Arg
        115                 120                 125

Gln Leu Ala His Asp Tyr Ser Lys Tyr Phe Ser Val Thr Glu Asp Leu
    130                 135                 140

Lys Arg Gln Ile Ile Ser Val Thr Thr Cys Asn Ala Ser Ile Val Leu
145                 150                 155                 160

Gln Asn Glu Asn Ala Arg Leu Thr Ala Asp Asp Phe Arg Leu Lys Cys
                165                 170                 175

Glu Asn Glu Leu Ala Leu His Gln Ser Val Glu Ala Asp Ile Asn Gly
            180                 185                 190

Leu His Arg Val Met Asp Glu Leu Thr Leu Cys Thr Ser Asp Leu Glu
        195                 200                 205

Met Gln Cys Glu Ala Leu Ser Glu Glu Leu Thr Tyr Leu Lys Lys Asn
    210                 215                 220

His Gln Glu Glu Met Lys Val Met Gln Gly Ala Ala Arg Gly Asn Val
225                 230                 235                 240

Asn Val Glu Ile Asn Ala Ala Pro Gly Val Asp Leu Thr Val Leu Leu
                245                 250                 255

Asn Asn Met Arg Ala Glu Tyr Glu Asp Leu Ala Glu Gln Asn His Glu
            260                 265                 270

Asp Ala Glu Ala Trp Phe Ser Glu Lys Ser Thr Ser Leu His Gln Gln
        275                 280                 285

Ile Ser Asp Asp Ala Gly Ala Ala Met Ala Ala Arg Asn Glu Leu Met
    290                 295                 300

Glu Leu Lys Arg Asn Leu Gln Thr Leu Glu Ile Glu Leu Gln Ser Leu
305                 310                 315                 320

Leu Ala Met Lys His Ser Tyr Glu Cys Ser Leu Ala Glu Thr Glu Ser
                325                 330                 335

Asn Tyr Cys His Gln Leu Gln Gln Ile Gln Glu Gln Ile Gly Ala Met
            340                 345                 350

Glu Asp Gln Leu Gln Gln Ile Arg Met Glu Thr Glu Gly Gln Lys Leu
        355                 360                 365

Glu His Glu Arg Leu Leu Asp Val Lys Ile Phe Leu Glu Lys Glu Ile
    370                 375                 380

Glu Met Tyr Cys Lys Leu Ile Asp Gly Glu Gly Arg Lys Ser Lys Ser
385                 390                 395                 400

Thr Cys Tyr Lys Ser Glu Gly Arg Gly Pro Lys Asn Ser Glu Asn Gln
                405                 410                 415

Val Lys Asp Ser Lys Glu Glu Ala Val Val Lys Thr Val Val Gly Glu
            420                 425                 430

Leu Asp Gln Leu Gly Ser Val Leu Ser Leu Arg Val His Ser Val Glu
        435                 440                 445

Glu Lys Ser Ser Lys Ile Ser Asn Ile Thr Met Glu Gln Arg Leu Pro
    450                 455                 460

Ser Lys Val Pro
465
```

<210> SEQ ID NO 3
<211> LENGTH: 16
<212> TYPE: DNA
<213> ORGANISM: Artificial Sequence
<220> FEATURE:
<223> OTHER INFORMATION: RBS1

<400> SEQUENCE: 3
aagaaggata tatcag                                                      16

<210> SEQ ID NO 4
<211> LENGTH: 2375
<212> TYPE: PRT
<213> ORGANISM: Artificial Sequence
<220> FEATURE:
<223> OTHER INFORMATION: PRT799

<400> SEQUENCE: 4

Met His His His His His Ser Ser Gly Ser Gly Pro Gly Gln
1               5                   10                  15

Gln Gly Pro Tyr Gly Pro Gly Ala Ser Ala Ala Ala Gly Gln
            20                  25                  30

Asn Gly Pro Gly Ser Gly Gln Gln Gly Pro Gln Ser Gly Gln Tyr
            35                  40                  45

Gly Pro Gly Gln Gln Gly Pro Gly Gln Gln Gly Pro Gly Ser Ser Ala
    50                  55                  60

Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Gly
            130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Gln Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ala Ala Ala Ala
            245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

Gln Gly Pro Gly Gln Ser Ala Ala Ala Ala Gly Pro Gly Gln Gln
            290                 295                 300

```
Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gly Pro Tyr Gly Pro Gly Gln
        355                 360                 365

Ser Ala Ala Ala Ala Gly Gln Tyr Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
            405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Tyr Gly Pro Gly Gln Ser
        435                 440                 445

Gly Pro Gly Ser Gly Gln Gln Gly Gln Gly Pro Tyr Gly Pro Gly Ala
450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala
            515                 520                 525

Gly Gln Tyr Gln Gln Gly Pro Gly Gln Gly Pro Tyr Gly Pro Gly
        530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser Gly Gln Gln Gly Pro Tyr Gly
        595                 600                 605

Pro Gly Ala Ser Ala Ala Ala Ala Gly Gln Asn Gly Pro Gly Ser
610                 615                 620

Gly Gln Gln Gly Pro Gly Gln Ser Gly Gln Tyr Gly Pro Gly Gln Gln
625                 630                 635                 640

Gly Pro Gly Gln Gln Gly Pro Gly Ser Ser Ala Ala Ala Ala Gly
            645                 650                 655

Pro Gly Gln Tyr Gly Pro Gly Gln Gly Pro Ser Ala Ser Ala Ala
            660                 665                 670

Ala Ala Ala Gly Pro Gly Ser Gly Gln Gln Gly Pro Gly Ala Ser Gly
        675                 680                 685

Gln Tyr Gly Pro Gly Gln Gln Gly Pro Gly Gln Gly Pro Gly Ser
        690                 695                 700

Ser Ala Ala Ala Ala Gly Gln Tyr Gly Ser Gly Pro Gly Gln Gln
705                 710                 715                 720

Gly Pro Tyr Gly Ser Ala Ala Ala Ala Ala Gly Pro Gly Ser Gly Gln
```

```
                725                 730                 735
Tyr Gly Gln Gly Pro Tyr Gly Pro Gly Ala Ser Gly Pro Gly Gln Tyr
                740                 745                 750
Gly Pro Gly Gln Gln Gly Pro Ser Ala Ser Ala Ala Ala Ala Ala Gly
                755                 760                 765
Ser Gly Gln Gln Gly Pro Gly Gln Tyr Gly Pro Tyr Ala Ser Ala Ala
                770                 775                 780
Ala Ala Ala Gly Gln Tyr Gly Ser Gly Pro Gly Gln Gln Gly Pro Tyr
785                 790                 795                 800
Gly Pro Gly Gln Ser Gly Ser Gly Gln Gln Gly Pro Gly Gln Gln Gly
                805                 810                 815
Pro Tyr Ala Ser Ala Ala Ala Ala Gly Pro Gly Gln Gln Gly Pro
                820                 825                 830
Tyr Gly Pro Gly Ser Ser Ala Ala Ala Ala Gly Gln Tyr Gly Tyr
                835                 840                 845
Gly Pro Gly Gln Gln Gly Pro Tyr Gly Pro Gly Ala Ser Gly Gln Asn
850                 855                 860
Gly Pro Gly Ser Gly Gln Tyr Gly Pro Gly Gln Gln Gly Pro Gly Gln
865                 870                 875                 880
Ser Ala Ala Ala Ala Ala Gly Pro Gly Gln Gln Gly Pro Tyr Gly Pro
                885                 890                 895
Gly Ala Ser Ala Ala Ala Ala Gly Gln Tyr Gly Pro Gly Gln Gln
                900                 905                 910
Gly Pro Gly Gln Tyr Gly Pro Gly Ser Ser Gly Pro Gly Gln Gln Gly
                915                 920                 925
Pro Tyr Gly Pro Gly Ser Ser Ala Ala Ala Ala Gly Gln Tyr Gly
                930                 935                 940
Pro Gly Gln Gln Gly Pro Tyr Gly Pro Gly Gln Ser Ala Ala Ala Ala
945                 950                 955                 960
Ala Gly Gln Tyr Gln Gln Gly Pro Gly Gln Gln Gly Pro Tyr Gly Pro
                965                 970                 975
Gly Ala Ser Gly Pro Gly Gln Gln Gly Pro Tyr Gly Pro Gly Ala Ser
                980                 985                 990
Ala Ala Ala Ala Ala Gly Pro Gly Gln Tyr Gly Pro Gly Gln Gln Gly
                995                1000                1005
Pro Ser Ala Ser Ala Ala Ala Ala Gly Gln Tyr Gly Ser Gly
                1010                1015                1020
Pro Gly Gln Tyr Gly Pro Tyr Gly Pro Gly Gln Ser Gly Pro Gly
                1025                1030                1035
Ser Gly Gln Gln Gly Gln Gly Pro Tyr Gly Pro Gly Ala Ser Ala
                1040                1045                1050
Ala Ala Ala Ala Gly Gln Tyr Gly Pro Gly Gln Gln Gly Pro Tyr
                1055                1060                1065
Gly Pro Gly Gln Ser Ala Ala Ala Ala Ala Gly Pro Gly Ser Gly
                1070                1075                1080
Gln Tyr Gly Pro Gly Ala Ser Gly Gln Asn Gly Pro Gly Ser Gly
                1085                1090                1095
Gln Tyr Gly Pro Gly Gln Gln Gly Pro Gly Gln Ser Ala Ala Ala
                1100                1105                1110
Ala Ala Gly Gln Tyr Gln Gln Gly Pro Gly Gln Gln Gly Pro Tyr
                1115                1120                1125
Gly Pro Gly Ala Ser Ala Ala Ala Ala Ala Gly Gln Tyr Gly Ser
                1130                1135                1140
```

-continued

Gly Pro Gly Gln Gly Pro Tyr Gly Pro Gly Gln Ser Gly Ser
1145                1150                1155

Gly Gln Gln Gly Pro Gly Gln Gln Gly Pro Tyr Ala Ser Ala Ala
1160                1165                1170

Ala Ala Ala Gly Pro Gly Ser Gly Gln Gln Gly Pro Gly Ala Ser
1175                1180                1185

Gly Gln Gln Gly Pro Tyr Gly Pro Gly Ala Ser Ala Ala Ala
1190                1195                1200

Ala Gly Gln Asn Gly Pro Gly Ser Gly Gln Gln Gly Pro Gly Gln
1205                1210                1215

Ser Gly Gln Tyr Gly Pro Gly Gln Gln Gly Pro Gly Gln Gln Gly
1220                1225                1230

Pro Gly Ser Ser Ala Ala Ala Ala Gly Pro Gly Gln Tyr Gly
1235                1240                1245

Pro Gly Gln Gln Gly Pro Ser Ala Ser Ala Ala Ala Ala Gly
1250                1255                1260

Pro Gly Ser Gly Gln Gln Gly Pro Gly Ala Ser Gly Gln Tyr Gly
1265                1270                1275

Pro Gly Gln Gln Gly Pro Gly Gln Gln Gly Pro Gly Ser Ser Ala
1280                1285                1290

Ala Ala Ala Ala Gly Gln Tyr Gly Ser Gly Pro Gly Gln Gln Gly
1295                1300                1305

Pro Tyr Gly Ser Ala Ala Ala Ala Gly Pro Gly Ser Gly Gln
1310                1315                1320

Tyr Gly Gln Gly Pro Tyr Gly Pro Gly Ala Ser Gly Pro Gly Gln
1325                1330                1335

Tyr Gly Pro Gly Gln Gln Gly Pro Ser Ala Ser Ala Ala Ala Ala
1340                1345                1350

Ala Gly Ser Gly Gln Gln Gly Pro Gly Gln Tyr Gly Pro Tyr Ala
1355                1360                1365

Ser Ala Ala Ala Ala Gly Gln Tyr Gly Ser Gly Pro Gly Gln
1370                1375                1380

Gln Gly Pro Tyr Gly Pro Gly Gln Ser Gly Ser Gly Gln Gln Gly
1385                1390                1395

Pro Gly Gln Gln Gly Pro Tyr Ala Ser Ala Ala Ala Ala Gly
1400                1405                1410

Pro Gly Gln Gln Gly Pro Tyr Gly Pro Gly Ser Ser Ala Ala Ala
1415                1420                1425

Ala Ala Gly Gln Tyr Gly Tyr Gly Pro Gly Gln Gln Gly Pro Tyr
1430                1435                1440

Gly Pro Gly Ala Ser Gly Gln Asn Gly Pro Gly Ser Gly Gln Tyr
1445                1450                1455

Gly Pro Gly Gln Gln Gly Pro Gly Gln Ser Ala Ala Ala Ala Ala
1460                1465                1470

Gly Pro Gly Gln Gln Gly Pro Tyr Gly Pro Gly Ala Ser Ala Ala
1475                1480                1485

Ala Ala Ala Gly Gln Tyr Gly Pro Gly Gln Gln Gly Pro Gly Gln
1490                1495                1500

Tyr Gly Pro Gly Ser Ser Gly Pro Gly Gln Gln Gly Pro Tyr Gly
1505                1510                1515

Pro Gly Ser Ser Ala Ala Ala Ala Ala Gly Gln Tyr Gly Pro Gly
1520                1525                1530

-continued

Gln Gln Gly Pro Tyr Gly Pro Gly Gln Ser Ala Ala Ala Ala Ala
1535                1540                1545

Gly Gln Tyr Gln Gln Gly Pro Gly Gln Gln Gly Pro Tyr Gly Pro
1550                1555                1560

Gly Ala Ser Gly Pro Gly Gln Gln Gly Pro Tyr Gly Pro Gly Ala
1565                1570                1575

Ser Ala Ala Ala Ala Ala Gly Pro Gly Gln Tyr Gly Pro Gly Gln
1580                1585                1590

Gln Gly Pro Ser Ala Ser Ala Ala Ala Ala Gly Gln Tyr Gly
1595                1600                1605

Ser Gly Pro Gly Gln Tyr Gly Pro Tyr Gly Pro Gly Gln Ser Gly
1610                1615                1620

Pro Gly Ser Gly Gln Gln Gly Gln Gly Pro Tyr Gly Pro Gly Ala
1625                1630                1635

Ser Ala Ala Ala Ala Ala Gly Gln Tyr Gly Pro Gly Gln Gln Gly
1640                1645                1650

Pro Tyr Gly Pro Gly Gln Ser Ala Ala Ala Ala Gly Pro Gly
1655                1660                1665

Ser Gly Gln Tyr Gly Pro Gly Ala Ser Gly Gln Asn Gly Pro Gly
1670                1675                1680

Ser Gly Gln Tyr Gly Pro Gly Gln Gln Gly Pro Gly Gln Ser Ala
1685                1690                1695

Ala Ala Ala Ala Gly Gln Tyr Gln Gln Gly Pro Gly Gln Gln Gly
1700                1705                1710

Pro Tyr Gly Pro Gly Ala Ser Ala Ala Ala Ala Gly Gln Tyr
1715                1720                1725

Gly Ser Gly Pro Gly Gln Gln Gly Pro Tyr Gly Pro Gly Gln Ser
1730                1735                1740

Gly Ser Gly Gln Gln Gly Pro Gly Gln Gln Pro Tyr Ala Ser
1745                1750                1755

Ala Ala Ala Ala Ala Gly Pro Gly Ser Gly Gln Gln Gly Pro Gly
1760                1765                1770

Ala Ser Gly Gln Gln Gly Pro Tyr Gly Pro Gly Ala Ser Ala Ala
1775                1780                1785

Ala Ala Ala Gly Gln Asn Gly Pro Gly Ser Gly Gln Gln Gly Pro
1790                1795                1800

Gly Gln Ser Gly Gln Tyr Gly Pro Gly Gln Gln Gly Pro Gly Gln
1805                1810                1815

Gln Gly Pro Gly Ser Ser Ala Ala Ala Ala Gly Pro Gly Gln
1820                1825                1830

Tyr Gly Pro Gly Gln Gln Gly Pro Ser Ala Ser Ala Ala Ala Ala
1835                1840                1845

Ala Gly Pro Gly Ser Gly Gln Gln Gly Pro Gly Ala Ser Gly Gln
1850                1855                1860

Tyr Gly Pro Gly Gln Gln Gly Pro Gly Gln Gln Gly Pro Gly Ser
1865                1870                1875

Ser Ala Ala Ala Ala Ala Gly Gln Tyr Gly Ser Gly Pro Gly Gln
1880                1885                1890

Gln Gly Pro Tyr Gly Ser Ala Ala Ala Ala Gly Pro Gly Ser
1895                1900                1905

Gly Gln Tyr Gly Gln Gly Pro Tyr Gly Pro Gly Ala Ser Gly Pro
1910                1915                1920

Gly Gln Tyr Gly Pro Gly Gln Gln Gly Pro Ser Ala Ser Ala Ala

-continued

```
              1925                1930                1935
Ala  Ala  Ala  Gly  Ser  Gly  Gln  Gln  Gly  Pro  Gly  Gln  Tyr  Gly  Pro
              1940                1945                1950
Tyr  Ala  Ser  Ala  Ala  Ala  Ala  Gly  Gln  Tyr  Gly  Ser  Gly  Pro
              1955                1960                1965
Gly  Gln  Gln  Gly  Pro  Tyr  Gly  Pro  Gly  Gln  Ser  Gly  Ser  Gly  Gln
              1970                1975                1980
Gln  Gly  Pro  Gly  Gln  Gln  Gly  Pro  Tyr  Ala  Ser  Ala  Ala  Ala  Ala
              1985                1990                1995
Ala  Gly  Pro  Gly  Gln  Gln  Gly  Pro  Tyr  Gly  Pro  Gly  Ser  Ser  Ala
              2000                2005                2010
Ala  Ala  Ala  Ala  Gly  Gln  Tyr  Gly  Tyr  Gly  Pro  Gly  Gln  Gln  Gly
              2015                2020                2025
Pro  Tyr  Gly  Pro  Gly  Ala  Ser  Gly  Gln  Asn  Gly  Pro  Gly  Ser  Gly
              2030                2035                2040
Gln  Tyr  Gly  Pro  Gly  Gln  Gln  Gly  Pro  Gly  Gln  Ser  Ala  Ala  Ala
              2045                2050                2055
Ala  Ala  Gly  Pro  Gly  Gln  Gln  Gly  Pro  Tyr  Gly  Pro  Gly  Ala  Ser
              2060                2065                2070
Ala  Ala  Ala  Ala  Ala  Gly  Gln  Tyr  Gly  Pro  Gly  Gln  Gln  Gly  Pro
              2075                2080                2085
Gly  Gln  Tyr  Gly  Pro  Gly  Ser  Ser  Gly  Pro  Gly  Gln  Gln  Gly  Pro
              2090                2095                2100
Tyr  Gly  Pro  Gly  Ser  Ser  Ala  Ala  Ala  Ala  Gly  Gln  Tyr  Gly
              2105                2110                2115
Pro  Gly  Gln  Gln  Gly  Pro  Tyr  Gly  Pro  Gly  Gln  Ser  Ala  Ala  Ala
              2120                2125                2130
Ala  Ala  Gly  Gln  Tyr  Gln  Gln  Gly  Pro  Gly  Gln  Gln  Gly  Pro  Tyr
              2135                2140                2145
Gly  Pro  Gly  Ala  Ser  Gly  Pro  Gly  Gln  Gln  Gly  Pro  Tyr  Gly  Pro
              2150                2155                2160
Gly  Ala  Ser  Ala  Ala  Ala  Ala  Gly  Pro  Gly  Gln  Tyr  Gly  Pro
              2165                2170                2175
Gly  Gln  Gln  Gly  Pro  Ser  Ala  Ser  Ala  Ala  Ala  Ala  Gly  Gln
              2180                2185                2190
Tyr  Gly  Ser  Gly  Pro  Gly  Gln  Tyr  Gly  Pro  Tyr  Gly  Pro  Gly  Gln
              2195                2200                2205
Ser  Gly  Pro  Gly  Ser  Gly  Gln  Gln  Gly  Gln  Gly  Pro  Tyr  Gly  Pro
              2210                2215                2220
Gly  Ala  Ser  Ala  Ala  Ala  Ala  Gly  Gln  Tyr  Gly  Pro  Gly  Gln
              2225                2230                2235
Gln  Gly  Pro  Tyr  Gly  Pro  Gly  Gln  Ser  Ala  Ala  Ala  Ala  Ala  Gly
              2240                2245                2250
Pro  Gly  Ser  Gly  Gln  Tyr  Gly  Pro  Gly  Ala  Ser  Gly  Gln  Asn  Gly
              2255                2260                2265
Pro  Gly  Ser  Gly  Gln  Tyr  Gly  Pro  Gly  Gln  Gln  Gly  Pro  Gly  Gln
              2270                2275                2280
Ser  Ala  Ala  Ala  Ala  Ala  Gly  Gln  Tyr  Gln  Gln  Gly  Pro  Gly  Gln
              2285                2290                2295
Gln  Gly  Pro  Tyr  Gly  Pro  Gly  Ala  Ser  Ala  Ala  Ala  Ala  Ala  Gly
              2300                2305                2310
Gln  Tyr  Gly  Ser  Gly  Pro  Gly  Gln  Gln  Gly  Pro  Tyr  Gly  Pro  Gly
              2315                2320                2325
```

Gln Ser Gly Ser Gly Gln Gln Gly Pro Gly Gln Gly Pro Tyr
    2330                2335                2340

Ala Ser Ala Ala Ala Ala Ala Gly Pro Gly Ser Gly Gln Gln Gly
    2345                2350                2355

Ser Ser Val Asp Lys Leu Ala Ala Ala Leu Glu His His His
    2360                2365                2370

His His
    2375

<210> SEQ ID NO 5
<211> LENGTH: 318
<212> TYPE: DNA
<213> ORGANISM: Artificial Sequence
<220> FEATURE:
<223> OTHER INFORMATION: S' holin (Enterobacteria phage lambda) coding
      gene

<400> SEQUENCE: 5
atgccagaaa aacatgacct gttggccgcc attctcgcgg caaaggaaca aggcatcggg    60
gcaatccttg cgtttgcaat ggcgtacctt cgcggcagat ataatggcgg tgcgtttaca   120
aaaacagtaa tcgacgcaac gatgtgcgcc attatcgcct ggttcattcg tgaccttctc   180
gacttcgccg actaagtag caatctcgct tatataacga gcgtgtttat cggctacatc    240
ggtactgact cgattggttc gcttatcaaa cgcttcgctg ctaaaaagc cggagtagaa    300 gatggtagaa atcaataa                                                  318

<210> SEQ ID NO 6
<211> LENGTH: 473
<212> TYPE: DNA
<213> ORGANISM: Artificial Sequence
<220> FEATURE:
<223> OTHER INFORMATION: R endolysin (Enterobacteria phage lambda)
      coding gene

<400> SEQUENCE: 6
atggtagaaa tcaataatca acgtaaggcg ttcctcgata tgctggcgtg gtcggaggga    60
actgataacg gacgtcagaa aaccagaaat catggttatg acgtcattgt aggcggagag   120
ctatttactg attactccga tcaccctcgc aaacttgtca cgctaaaccc aaaactcaaa   180
tcaacaggcg ccggacgcta ccagcttctt tcccgttggt gggatgccta ccgcaagcag   240
cttggcctga agacttctc tccgaaaagt caggacgctg tggcattgca gcagattaag   300
gagcgtggcg ctttacctat gattgatcgt ggtgatatcc gtcaggcaat cgaccgttgc   360
agcaatatct gggcttcact gccgggcgct ggttatggtc agttcgagca taaggctgac   420
agcctgattg caaaattcaa agaagcgggc ggaacggtca gagagattga tgt          473

<210> SEQ ID NO 7
<211> LENGTH: 462
<212> TYPE: DNA
<213> ORGANISM: Artificial Sequence
<220> FEATURE:
<223> OTHER INFORMATION: Rz cell lysis protein (Enterobacteria phage
      lambda) coding gene

<400> SEQUENCE: 7
atgagcagag tcaccgcgat tatctccgct ctggttatct gcatcatcgt ctgcctgtca    60
tgggctgtta atcattaccg tgataacgcc attacctaca aagcccagcg cgacaaaaat   120
gccagagaac tgaagctggc gaacgcggca attactgaca tgcagatgcg tcagcgtgat   180

```
gttgctgcgc tcgatgcaaa atacacgaag gagttagctg atgctaaagc tgaaaatgat      240
gctctgcgtg atgatgttgc cgctggtcgt cgtcggttgc acatcaaagc agtctgtcag      300
tcagtgcgtg aagccaccac cgcctccggc gtggataatg cagcctcccc ccgactggca      360
gacaccgctg aacgggatta tttcaccctc agagagaggc tgatcactat gcaaaaacaa      420
ctggaaggaa cccagaagta tattaatgag cagtgcagat ag                        462
```

<210> SEQ ID NO 8  
<211> LENGTH: 1236  
<212> TYPE: DNA  
<213> ORGANISM: Artificial Sequence  
<220> FEATURE:  
<223> OTHER INFORMATION: lambda-SRRz

<400> SEQUENCE: 8

```
atgccagaaa acatgacct gttggccgcc attctcgcgg caaaggaaca aggcatcggg        60
gcaatccttg cgtttgcaat ggcgtacctt cgcggcagat ataatggcgg tgcgtttaca      120
aaaacagtaa tcgacgcaac gatgtgcgcc attatcgcct agttcattcg tgaccttctc      180
gacttcgccg gactaagtag caatctcgct tatataacga gcgtgtttat cggctacatc      240
ggtactgact cgattggttc gcttatcaaa cgcttcgctg ctaaaaaagc cggagtagaa      300
gatggtagaa atcaataatc aacgtaaggc gttcctcgat atgctggcgt ggtcggaggg      360
aactgataac ggacgtcaga aaccagaaa tcatggttat gacgtcattg taggcggaga      420
gctatttact gattactccg atcaccctcg caaacttgtc acgctaaacc caaaactcaa      480
atcaacaggc gccggacgct accagcttct ttcccgttgg tgggatgcct accgcaagca      540
gcttggcctg aaagacttct ctccgaaaag tcaggacgct gtggcattgc agcagattaa      600
ggagcgtggc gctttaccta tgattgatcg tggtgatatc cgtcaggcaa tcgaccgttg      660
cagcaatatc tgggcttcac tgccgggcgc tggttatggt cagttcgagc ataaggctga      720
cagcctgatt gcaaaattca agaagcgggc ggaacggtc agagagattg atgtatgagc      780
agagtcaccg cgattatctc cgctctggtt atctgcatca tcgtctgcct gtcatgggct      840
gttaatcatt accgtgataa cgccattacc tacaaagccc agcgcgacaa aaatgccaga      900
gaactgaagc tggcgaacgc ggcaattact gacatgcaga tgcgtcagcg tgatgttgct      960
gcgctcgatg caaaatacac gaaggagtta gctgatgcta agctgaaaaa tgatgctctg     1020
cgtgatgatg ttgccgctgg tcgtcgtcgg ttgcacatca aagcagtctg tcagtcagtg     1080
cgtgaagcca ccaccgcctc cggcgtggat aatgcagcct cccccgact ggcagacacc     1140 gctgaacggg attatttcac cctcagagag aggctgatca ctatgcaaaa acaactggaa     1200
ggaacccaga gtatattaa tgagcagtgc agatag                                1236
```

<210> SEQ ID NO 9  
<211> LENGTH: 17  
<212> TYPE: DNA  
<213> ORGANISM: Artificial Sequence  
<220> FEATURE:  
<223> OTHER INFORMATION: RBS2

<400> SEQUENCE: 9

```
aagaaggcta tatacag                                                      17
```

<210> SEQ ID NO 10  
<211> LENGTH: 17  
<212> TYPE: DNA

```
<213> ORGANISM: Artificial Sequence
<220> FEATURE:
<223> OTHER INFORMATION: RBS3

<400> SEQUENCE: 10
aagaagtcta tatacag                                                    17

<210> SEQ ID NO 11
<211> LENGTH: 17
<212> TYPE: DNA
<213> ORGANISM: Artificial Sequence
<220> FEATURE:
<223> OTHER INFORMATION: RBS4

<400> SEQUENCE: 11
aagctttcta tatacag                                                    17

<210> SEQ ID NO 12
<211> LENGTH: 17
<212> TYPE: DNA
<213> ORGANISM: Artificial Sequence
<220> FEATURE:
<223> OTHER INFORMATION: RBS5

<400> SEQUENCE: 12
tgcgtttcta tatacag                                                    17

<210> SEQ ID NO 13
<211> LENGTH: 45
<212> TYPE: DNA
<213> ORGANISM: Artificial Sequence
<220> FEATURE:
<223> OTHER INFORMATION: Primer

<400> SEQUENCE: 13
ttgaggggtt ttttgaagaa ggatatatac agatgccaga aaaac                     45

<210> SEQ ID NO 14
<211> LENGTH: 51
<212> TYPE: DNA
<213> ORGANISM: Artificial Sequence
<220> FEATURE:
<223> OTHER INFORMATION: Primer

<400> SEQUENCE: 14
agttcctcct ttcagccatg gaagcttgca tgcctgcagg tcgactctag a              51

<210> SEQ ID NO 15
<211> LENGTH: 786
<212> TYPE: DNA
<213> ORGANISM: Artificial Sequence
<220> FEATURE:
<223> OTHER INFORMATION: DNase1 coding gene

<400> SEQUENCE: 15
atgctgaaga tagcagcctt caacatccgc accttggggg agaccaagat gtccaatgct     60
acgctcgcca gctacattgt tcggatcgtg cgtcgttacg acatcgtcct catccaggag    120
gtcagagaca gccacctggt ggctgtgggg aagctcctgg actatctcaa ccaggatgac    180
ccaaacacct accactatgt ggtcagtgag ccgctgggcc gcaacagcta aaggagcgc    240 tacctctttc tgttcagacc caacaaggtg tccgtgctgg acacctacca gtacgacgac    300
ggctgcgagt cctgcgggaa cgacagcttc agcgggagc cgctgtggt caagttctca    360 tcccactcca ccaaggtcaa ggaatttgcc attgttgccc tgcactcggc cccatcggac    420
```

```
gcagtggctg agattaattc tctctacgat gtctacctgg atgtccagca gaagtggcac    480
ttgaacgatg tcatgttgat gggcgatttc aatgctgact gcagctacgt gacctcctcg    540
cagtggtcat ccatccgcct gcgtacgagc tccaccttcc agtggctgat tcctgacagt    600
gccgacacca cggctacgtc cacgaactgc gcctatgaca ggatcgtggt cgcagggtct    660
ctgctccaga gttctgtggt tcctggctcg gccgctccct ttgacttcca agctgcatac    720
ggactgagca atgagatggc cctggccatc agtgaccatt acccggtgga ggtgacgctg    780
acataa                                                              786
```

EXPRESSION CASSETTE

SEQUENCE LISTING SUBMISSION VIA EFS-WEB

A computer readable text file, entitled "SequenceListing.txt," created on or about Mar. 23, 2020 with a file size of about 34 kb contains the sequence listing for this application and is hereby incorporated by reference in its entirety.

TECHNICAL FIELD

The present invention relates to expression cassettes, particularly relates to expression cassettes for expressing a plurality of genes including a gene encoding a protein of interest.

BACKGROUND ART

Many expression systems for heterologous expression, such as recombinant proteins, have been studied. When expressing a protein of interest, the level or timing of expression of a gene which is different from a gene encoding the protein of interest is sometimes controlled in the same cell. For example, when expressing a protein of interest and a lytic enzyme that lyses a cell, it is desirable that the lytic enzyme be expressed in an amount capable of lysing the cell at a timing when the protein of interest is obtained in a desired amount.

As a system for expressing a plurality of genes including a gene encoding a protein of interest in the same cell, for example, a system of inducing an expression of another gene under another promoter control after expressing a protein of interest in a desired amount is known (Patent Literature 1). However, in this method, another gene that is different from the gene encoding the protein of interest sometimes fails to be expressed in the desired amount. For example, if a protein other than the protein of interest is a cytolytic enzyme, there is a problem that, after expressing the protein of interest in the desired amount, attempting to induce expression of the cytolytic enzyme fails to reach the amount capable of lysing the host cell.

CITATION LIST

Patent Literature

Patent Literature 1: Japanese Unexamined Patent Publication No. 2003-219895

SUMMARY OF INVENTION

Technical Problem

The present invention is intended to provide an expression cassette capable of expressing a plurality of genes including a gene encoding a protein of interest and expressing genes other than the gene encoding the protein of interest in an amount lower than the gene encoding the protein of interest.

Solution to Problem

The present inventors have found that expression cassettes which are driven by one promoter, include a first nucleic acid and a second nucleic acid each containing a gene, and include a terminator between the first nucleic acid and the second nucleic acid allow the expression of the respective genes contained in the first nucleic acid and the second nucleic acid, and the expression level of the gene contained in the second nucleic acid downstream of the terminator is lower than the expression level of the gene contained in the first nucleic acid, and have completed the present invention.

That is, the present invention provides, for example, the following [1] to [18].

[1] An expression cassette comprising, in a 5' to 3' direction of a sense strand, a promoter, and a first nucleic acid, a terminator and a second nucleic acid operably linked to the promoter, wherein
the first nucleic acid and the second nucleic acid each contain at least one gene.
[2] The expression cassette according to [1], further comprising a modified ribosome binding site (RBS) at downstream of the terminator and upstream of the second nucleic acid.
[3] The expression cassette according to [1] or [2], wherein the first nucleic acid contains a gene encoding a protein of interest.
[4] The expression cassette according to [3], wherein the protein of interest is a structural protein.
[5] The expression cassette according to [4], wherein the structural protein is a protein selected from the group consisting of keratin, collagen, elastin, resilin, silkworm silk, and spider silk, or a protein derived therefrom.
[6] The expression cassette according to any one of [1] to [5], wherein the second nucleic acid contains a gene encoding a protein having a lysis activity on a host cell and/or a gene encoding a deoxyribonuclease.
[7] The expression cassette according to [6], wherein the gene encoding a protein having a lysis activity on a host cell is selected from the group consisting of a lysozyme gene, a VanX gene, an S gene, an R gene, and an Rz gene.
[8] The expression cassette according to [6], wherein the second nucleic acid contains the S gene, the R gene, and the Rz gene.
[9] The expression cassette according to any one of [6] to [8], wherein the gene encoding a deoxyribonuclease is a gene encoding DNase I.
[10] The expression cassette according to any one of [1] to [9], wherein the promoter is a T7 promoter.
[11] The expression cassette according to any one of [1] to [10], wherein the terminator is a T7 terminator.
[12] The expression cassette according to any one of [1] to [11], wherein an expression level of the gene contained in the second nucleic acid is 20% or less of an expression level of the gene contained in the first nucleic acid.
[13] A recombinant cell comprising the expression cassette according to any one of [3] to [12] introduced thereinto.
[14] A method for producing the recombinant cell according to [13], comprising introducing the expression cassette into a host cell using a plasmid.
[15] A method for producing the recombinant cell according to [13], wherein the expression cassette is introduced into a genomic DNA of a host cell.
[16] A method for producing a protein of interest, comprising culturing the recombinant cell according to [13] under conditions that enable the protein of interest to be expressed.
[17] The method according to [16], comprising activating the promoter by induction by a drug, induction by a temperature change, or induction by starvation.
[18] The method according to [17], wherein the induction by the drug is induction by IPTG.

Advantageous Effects of Invention

According to the present invention, a plurality of genes can be expressed under one promoter drive, and genes downstream of the terminator can be expressed less than those upstream. This, for example, reduces the expression level of the lytic enzyme as compared to the expression level of the protein of interest under one promoter drive, so that no cell lysis occurs before the desired amount of the protein of interest is expressed, resulting in obtaining an amount of lytic enzyme capable of lysing the cell after the desired amount of the protein of interest is expressed, and allowing the cell lysis to yield the desired amount of the protein of interest.

BRIEF DESCRIPTION OF DRAWINGS

FIG. 3 is a graph showing SSP concentrations relative to induction time. The abscissa shows the induction time (hr) and the ordinate shows the relative value for SSP concentration at 20 hours of the induction time of cassette 0.

FIG. 4 is a graph showing turbidity of the culture solution in OD600 relative to culture time. The abscissa shows the culture time (hr) and the ordinate shows the relative value for the turbidity of the culture solution in OD600 at 35 hours from the start of the culture of cassette 0.

DESCRIPTION OF EMBODIMENTS

Figure 1:
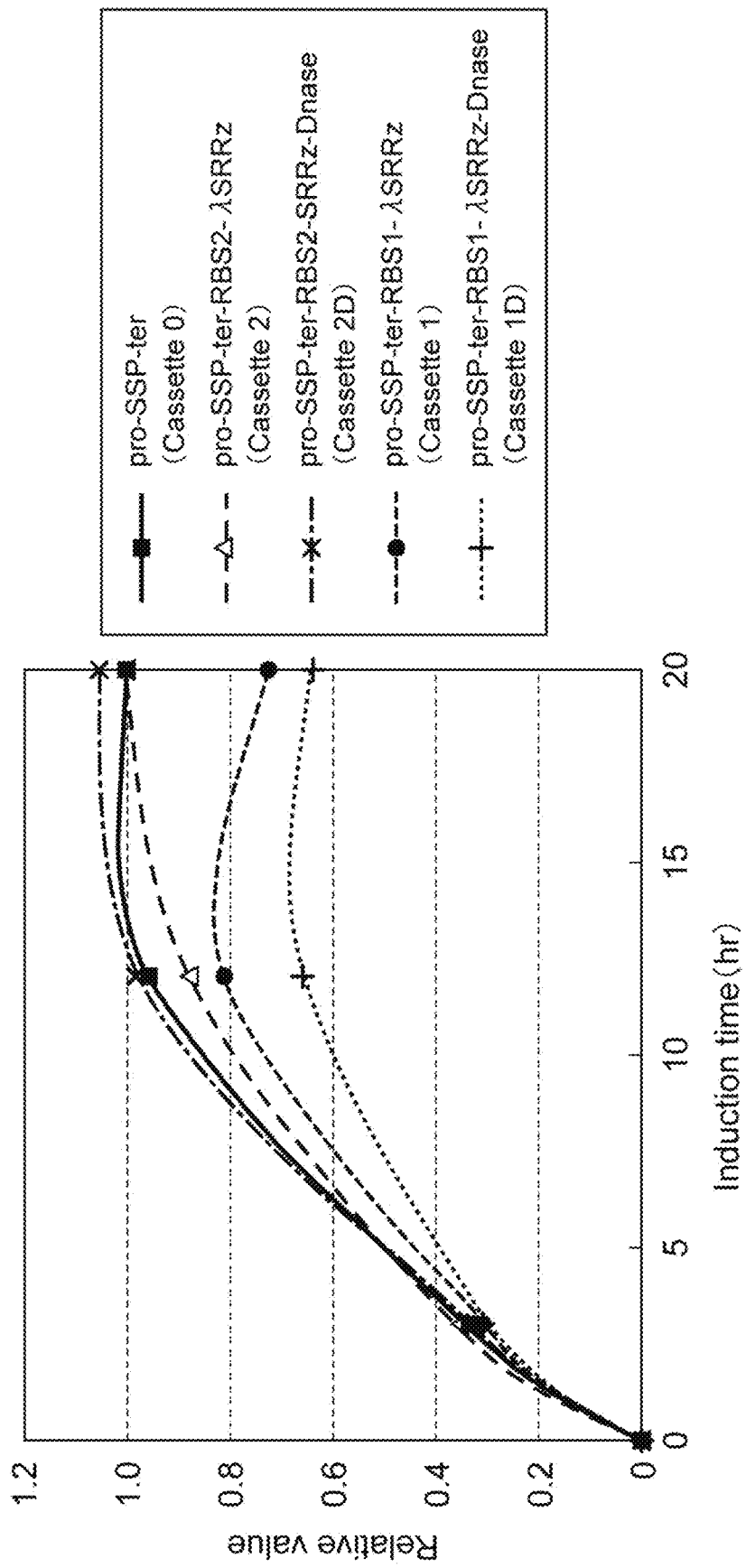
FIG. 1 is a graph showing spider silk protein (SSP) concentrations relative to induction time. The abscissa shows the induction time (hr) and the ordinate shows the relative value for SSP concentration at 20 hours of the induction time of cassette 0.

Hereinafter, the embodiments for carrying out the present invention are described in detail. However, the present invention is not limited to the following embodiments.
[Expression Cassette]

In the present invention, an expression cassette means a DNA fragment comprising a nucleic acid containing a gene and a promoter and a terminator linked to the nucleic acid. An expression cassette according to the present embodiment is an expression cassette comprising, in a 5' to 3' direction of a sense strand, a promoter, and a first nucleic acid, a terminator and a second nucleic acid operably linked to the promoter, wherein the first nucleic acid and the second nucleic acid each contain at least one gene.
[Promoter]

A promoter is not limited as long as it functions in a host cell. Examples of the promoter include a promoter derived from E. coli or phage such as a tip promoter (Ptrp), a lac promoter, a PL promoter, a PR promoter, and a T7 promoter; a promoter with two Ptrps in series (Pulp×2); a promoter artificially designed and engineered such as a tac promoter, a lacT7 promoter, a lacT7.1 promoter, a lacT7.2 promoter, a lacT7.3 promoter, a lacT7.4 promoter, a lacT7.5 promoter, and a let I promoter; an araBAD promoter, a rhaBAD promoter, a xylF promoter, a xylA promoter, a phoA promoter, a cstA promoter and a cstA-lacZ promoter, a promoter of genes of glycolysis such as hexokinase, a PHOS promoter, a PGK promoter, a GAP promoter, an ADH promoter, a gal 1 promoter, a gall 0 promoter; a heat shock polypeptide promoter, an MFa1 promoter, a CUP 1 promoter, a pGAP promoter, a pGCW14 promoter, an AOX1 promoter, and an MOX promoter.

It is preferable that the promoter is an expression-inducible promoter. The expression-inducible promoter can control transcription by presence of an inducing substance (expression inducer); absence of a repressor molecule; or physical factors such as increase or decrease in temperature, osmotic pressure, or pH value; or the like.

Examples of the expression-inducible promoters include T7 promoters, tac and trc promoters, lac and lacUV5 promoters, induced by lactose or its analog IPTG (isopropyl-thiol-β-D-galactoside); araRAD promoters induced by arabinose; trp promoters induced by β-indole acrylic acid addition or tryptophan starvation and inhibited by tryptophan addition; rhaBAD promoters induced by rhamnose; xylF and xylA promoters induced by xylose; lambda phage PR and PL promoters induced by temperature increase; phoA promoters induced by phosphate starvation; and cstA and cstA-lacZ promoters induced by glucose starvation. In the expression cassette of the present invention, it is preferable to use a T7 promoter.
[Terminator]

As terminators (transcriptional termination sequences), any of the nucleotide sequences that terminate transcription initiated by the promoter in the host cell can be used. It may be a terminator from prokaryotes or eukaryotes or a terminator from phages. Examples of the terminator from bacteriophages include T7 terminators, T3 terminators and SP6 terminators.

It is preferable to use a terminator corresponding to the promoter used, but the terminator is not limited thereto. As an example of the corresponding, if the promoter is a T7 promoter, it is preferable to use a T7 terminator.

Terminators may further be included other than between the first nucleic acid and the second nucleic acid, for example, may be included at downstream of the second nucleic acid. Terminators may or may not be included after the last gene transcribed by the above promoter.
[Nucleic Acid]

The expression cassette of the present invention comprises at least a first nucleic acid and a second nucleic acid. The present invention is not limited thereto, and the expression cassette can further comprise one or more nucleic acids. For example, the expression cassette of the present invention may further comprise a third nucleic acid.

The first nucleic acid and the second nucleic acid each contain at least one gene. The present invention is not limited thereto, and each nucleic acid may comprise two or more genes, and the two or more genes may be different or the same. The genes refer to specific regions on nucleic acid (DNA) molecules that contain information on transcripts corresponding to a primary structure of a protein or transcripts such as transcribed RNA (tRNA) or ribosomal RNA. The nucleic acids may also include, in addition to genes, for example, spacers, terminators, and ribosome binding sites (RBS).

Gene expression includes synthesis of proteins based on genetic information of genes and synthesis of transcripts (transcription) based on genetic information of genes.

The present invention has a terminator sequence between the first nucleic acid and the second nucleic acid. It is known that transcription is not completely terminated by the terminator and that 20 to 30% thereof is read through. Read through means that the transcription, which is originally to be terminated by the terminator, does not terminate, and further transcription continues. For T7 terminators, read through of about 30% is assumed to occur (Merck & Co., pET system manual, page 18).

The present invention utilizes this read through to control expression of genes after the terminator. That is, placing a terminator between the first nucleic acid and the second nucleic acid under one promoter drive reduces the number of copies transcribed of the gene contained in the second nucleic acids compared to that of the gene contained in the first nucleic acid, although the gene contained in the second nucleic acid is transcribed by read through. The lower the number of copies transcribed, the lower the expression level of the gene (if the gene is a gene encoding a protein, the number of molecules of the protein), so that the expression level of the gene contained in the second nucleic acid is lower than the expression level of the gene contained in the first nucleic acid. In the present invention, expression of the gene contained in the second nucleic acid is suppressed low, but not completely suppressed. Thus, transcription is not completely terminated by a terminator present between the first nucleic acid and the second nucleic acid downstream of one promoter sequence. The incomplete termination of transcription can be confirmed by RT-PCR or the like. The frequency of the read through can be calculated as the transcription amount of the gene contained in the second nucleic acid/the transcription amount of the gene contained in the first nucleic acid×100(%), or the expression level of the gene contained in the second nucleic acid/the expression level of the gene contained in the first nucleic acid×100(%). The transcription amount of each gene can be confirmed by RT-PCR or the like. The expression level of each gene can be confirmed by HPLC, SDS-PAGE, or the like. The frequency of the read through is preferably 10 to 40%, and more preferably 20 to 30%.

Because of the terminator sequence between the first nucleic acid and the second nucleic acid, expression of the genes contained in the second nucleic acid is suppressed by read through, as described above. Thus, it is preferable that the gene contained in the first nucleic acid whose expression is not suppressed by read through is a gene encoding a protein of interest. It is more preferable that the first nucleic acid contains a gene encoding a structural protein. It is preferable that the gene contained in the second nucleic acid whose expression is suppressed by read through is, for example, a gene sequence encoding a protein having activity to lyse a host cell and/or a gene encoding a deoxyribonuclease. It is also more preferable that the first nucleic acid contains a gene encoding a structural protein, and the second nucleic acid contains a gene encoding a protein having activity to lyse a host cell and/or a gene encoding a deoxyribonuclease.

[Protein]

A protein of interest means a protein that is intended to be expressed by a method of protein expression and then recovered and utilized, or the like. The protein of interest can include any protein that is preferably manufactured on an industrial scale, and examples thereof include proteins available for industrial use, proteins available for medical use, and structural proteins. Specific examples of the proteins available for industrial or medical use include enzymes, regulatory proteins, receptors, peptide hormones, cytokines, membrane or transport proteins, antigens for vaccination, vaccines, antigen-binding proteins, immunostimulatory proteins, allergens, and full-length antibodies, or antibody fragments or derivatives. Specific examples of the structural protein include fibroin (e.g., spider silk and silkworm silk), keratin, collagen, elastin, resillin, and fragments of these proteins, as well as proteins derived therefrom.

The spider silk or silkworm silk-derived protein, which is a fibroin-like protein, may be a naturally occurring protein (naturally occurring fibroin) or an artificially manufactured protein (modified fibroin), and examples thereof include a protein containing a domain sequence represented by formula 1: $[(A)_n$ motif-REP$]_m$ or formula 2: $[(A)_n$ motif-REP$]_m$-$(A)_n$ motif.

The modified fibroin may further contain an amino acid sequence added to either or both of the N- and C-terminal sides of the domain sequence (N- and C-terminal sequences). Examples of the N-terminal and C-terminal sequences include, but are not limited to, regions typically free of repeats of amino acid motifs characteristic to fibroin and consisting of about 100 residues of amino acids. The $(A)_n$ motif represents amino acid sequence predominantly containing alanine residues, and the number of amino acid residues ranges from 2 to 27. The number of amino acid residues in the $(A)_n$ motif may be an integer of 2 to 20, 4 to 27, 4 to 20, 8 to 20, 10 to 20, 4 to 16, 8 to 16, or 10 to 16. Furthermore, the ratio of the number of alanine residues to the total number of amino acid residues in the $(A)_n$ motif may be 40% or more, 60% or more, 70% or more, 80% or more, 83% or more, 85% or more, 86% or more, 90% or more, 95% or more, or 100% (meaning that it consists of only alanine residues). Among a plurality of $(A)_n$ motifs present in the domain sequence, at least seven motifs may consist of alanine residues only. REP represents an amino acid sequence consisting of 2 to 200 amino acid residues. The REP may be an amino acid sequence consisting of 10 to 200 amino acid residues. m represents an integer of 2 to 300 and may be an integer of 10 to 300. A plurality of $(A)_n$ motifs present may have the same amino acid sequence as one another or may have different amino acid sequences. A plurality of REPs present may have the same amino acid sequence as one another or may have different amino acid sequences. For example, the modified fibroin may be represented by formula 1: $[(A)_n$ motif-REM$]_m$ (wherein, in the formula 1, $(A)_n$ motif represents an amino acid sequence consisting of 4 to 20 amino acid residues and the number of alanine residues relative to the total number of amino acid residues in the $(A)_n$ motif is 80% or more. REP represents an amino acid sequence consisting of 10 to 200 amino acid residues. m represents an integer of 8 to 300. A plurality of $(A)_{11}$ motifs present may have the same amino acid sequence as one another or may have different amino acid sequences. A plurality of REPs present may have the same amino acid sequence as one another or may have different amino acid sequences).

The modified fibroin can be obtained, for example, by amino acid sequence modifications corresponding to the substitution, deletion, insertion and/or addition of one or more amino acid residues to a genetic sequence cloned naturally occurring fibroin. Substitutions, deletions, insertions and/or additions of amino acid residues can be made by methods well known to those skilled in the art, such as partially specific mutagenesis methods. Specifically, it can be performed in accordance with methods described in literatures such as Nucleic Acid Res. 10, 6487 (1982), Methods in Enzymology, 100, 448 (1983).

Examples of the naturally occurring fibroin include fibroin produced by spiders (spider silk) and fibroin produced by insects.

Examples of the spider silk include spider silk proteins produced by spiders belonging to the genus *Araneus* such as *Araneus ventricosus*, *Araneus diadematus*, *Araneus quadratus*, *Araneus pentagrammicus* and *Araneus nojimai*, spiders belonging to the genus *Neoscona* such as *Neoscona scylla*, *Neoscona nautica*, *Neoscona adianta* and *Neoscona scylloides*, spiders belonging to the genus *Pronus* such as

*Pronous minutus*, spiders belonging to the genus *Cyrtarachne* such as *Cyrtarachne bufo* and *Cyrtarachne inaequalis*, spiders belonging to the genus *Gasteracantha* such as *Gasteracantha kuhlii* and *Gasteracantha mammosa*, spiders belonging to the genus *Ordgarius* such as *Ordgarius hobsoni* and *Ordgarius sexspinosus*, spiders belonging to the genus *Argiope* such as *Argiope bruennichii*, *Argiope minuta*, and *Argiope bruennichii*, spiders belonging to the genus *Arachnura* such as *Arachnura logio*, spiders belonging to the genus *Acusilas* such as *Acusilas coccineus*, Spiders belonging to the genus *Cytophora* such as *Cyrtophora moluccensis*, *Cyrtophora exanthematica*, and *Cyrtophora unicolor*, spiders belonging to the genus *Poltys* such as *Poltys illepidus*, spiders belonging to the genus *Cyclosa* such as *Cyclosa octotuberculata*, *Cyclosa sedeculata*, *Cyclosa vallata*, and *Cyclosa atrata*, and spiders belonging to the genus *Chorizopes* such as *Chorizopes nipponicus*; and spider silk produced by spiders belonging to the family Tetragnathidae including spiders belonging to the genus *Tetragnatha* such as *Tetragnatha praedonia*, *Tetragnatha praedonia*, *Tetragnatha extensa*, *Tetragnatha squamata*, spiders belonging to the genus *Leucauge* such as *Leucauge celebesiana*, *Leucauge blanda*, and *Leucauge subblanda*, spiders belonging to the genus *Nephila* such as *Nephila clavata* and *Nephila pilipes*, spiders belonging to the genus *Menosira* such as *Menosira ornata*, spiders belonging to the genus *Dyschiriognatha* such as *Dyschiriognatha tenera*, spiders belonging to the genus *Latrodectus* such as *Latrodectus mactans*, *Latrodectus hasseltii*, *Latrodectus geometricus*, and *Latrodectus tredecimguttatus*; and spiders belonging to the genus *Euprosthenops*.

Examples of the fibroin produced by insect include silk proteins produced by silkworms such as *Bombyx mori*, *Bombyx mandarins*, *Antheraea yamamai*, *Antheraea pernyi*, *Eriogyna pyretorum*, *Pilosamia cynthia ricini*, *Sarnia cynthia*, *Caligura japonica*, *Antheraea mylitta*, *Antheraea assama*, and hornet silk protein released by larvae of *Vespa simillifna xanthoptera*.

Examples of the collagen-derived protein include a protein containing a domain sequence represented by formula 3: $[REP2]_o$, (wherein, in the formula 3, o represents an integer from 5 to 300; REP2 represents an amino acid sequence consisting of Gly-X-Y; X and Y represent any amino acid residue other than Gly; and a plurality of REP2 present may be the same amino acid sequence as one another or different amino acid sequences).

Examples of the resillin-derived protein include a protein containing a domain sequence represented by formula 4: $[REP3]_p$, (wherein, in the formula 4, p indicates an integer from 4 to 300; REP3 shows the amino acid sequence consisting of Ser-J-J-Tyr-Gly-U-Pro; J represents any amino acid residue, preferably an amino acid residue selected from the group consisting of Asp, Ser, and Thr; U represents any amino acid residue, preferably an amino acid residue selected from the group consisting of Pro, Ala, Thr and Ser; and a plurality of REP3 present may be the same amino acid sequence as one another or different amino acid sequences).

Examples of the elastin-derived protein include proteins having the amino acid sequence such as Accession No. AAC98395 (human), I47076 (sheep), NP786966 (bovine) of GenBank of NCBI. Specifically, a protein containing the amino acid sequence represented by SEQ ID NO: 1 can be listed.

Examples of the keratin-derived protein include type I keratin of *Capra hircus*. Specific examples thereof include a protein including an amino acid sequence of SEQ ID NO: 2 (amino acid sequence of accession number ACY30466 of GenBank, NCBI).

As discussed above, due to the read through, the expression level of a gene contained in the second nucleic acid is lower than that of a gene contained in the first nucleic acid. Thus, the expression level of a protein encoded by the gene contained in the second nucleic acid is also lower than that of a protein encoded by the gene contained in the first nucleic acid. The protein encoded by the gene contained in the second nucleic acid may be different from or the same as the protein encoded by the gene contained in the first nucleic acid. The gene contained in the second nucleic acid is not limited to only one type of gene, and may be two, three, four types of genes, and a plurality of genes.

Examples of the protein that suppresses expression levels include proteins that affect expression of a gene contained in the first nucleic acid. Specific examples thereof include hydrolases, nucleases, oxidoreductases, transferases, lyases, and isomerizing enzymes synthetases.

Examples of the hydrolases include lytic enzymes, proteases, amylases, and lipases.

The lytic enzyme is not particularly limited as long as it is a protein having activity to lyse a host cell. Examples thereof include holin, endolysine, pectinase, lysozyme, cellulase, zymolyase, and Driselase, which are cell wall degrading enzymes, and VanX having bacteriolytic activity involved in vancomycin resistance.

It is also known that a plurality of lytic enzymes (lytic enzyme group) work together to effectively lyse host cells. Thus, a plurality of genes encoding these enzymes may be included in a nucleic acid after (downstream of) the first nucleic acid, for example, in a second nucleic acid. Examples of the genes encoding enzymes which cooperate in this way to effectively lyse a host cell include SRRz of Enterobacteria phage lambda, consisting of the S gene encoding holin of Enterobacteria phage lambda (GeneID: 5740919 of GenBank, NCBI), the R gene encoding endolysin (GeneID: 2703480 of GenBank, NCBI), and the Rz gene encoding cell lysis protein (GeneID: 2703481 of GenBank, NCBI).

Thus, the second nucleic acid may contain one or more genes selected from the group consisting of lysozyme genes, VanX genes, S genes, R genes, and Rz genes. For example, the second nucleic acid may contain a sequence of the S gene, and the third nucleic acid included downstream thereof may contain a sequence of the R gene. Also, for example, the second nucleic acid may contain sequences of the S gene, the R gene, and the Rz gene.

Examples of the nucleases include deoxyribonuclease (DNase) and ribonuclease (RNase). Examples of DNase include TaqI from thermophilia, EndA from *E. coli* periplasm, and DNase I gene from bovine pancreas. In the present invention, it is preferable that the second nucleic acid contains a gene encoding a deoxyribonuclease, and more preferable that the second nucleic acid contains a DNase I gene. When expression cassettes are used to express proteins using transformed *E. coli*, nucleic acids such as DNA are eluted from the crushed *E. coli* bacteria and increase the viscosity of the treatment solution to cause troubles in subsequent steps, but such problems can also be solved by expressing DNase.

The expression level of the gene contained in the second nucleic acid is preferably 40% or less, more preferably 30% or less, and further preferably 20% or less relative to the expression level of the gene contained in the first nucleic acid. When the first nucleic acid contains a gene encoding a protein of interest, the expression level of a gene contained in the second nucleic acid is preferably 40% or less, more preferably 30% or less, and further preferably 20% or less relative to the expression level of the gene encoding the protein of interest. When the first nucleic acid contains a gene encoding a protein of interest and the second nucleic acid contains a gene or genes encoding a lytic enzyme or lytic enzyme group, it is preferable that the expression level of the gene or genes encoding a lytic enzyme or lytic enzyme group is 20% or less relative to the expression level of the gene encoding the protein of interest. The above-described expression level is preferable because the protein of interest is sufficiently expressed, and then the expression level of the gene contained in the second nucleic acid becomes sufficient for the protein or transcript synthesized based on the genetic information of the gene to function.

[Ribosome Binding Site (RBS)]

Ribosome binding sites (RBS) are sequences for binding ribosomes to initiate translation, located upstream of the translation initiation codon of each gene. By modifying this RBS sequence, expression of the downstream gene can be controlled. If the frequency of read through from the terminator is higher than desired frequency, modification of the RBS sequence can suppress expression of the downstream gene.

Modification of an RBS sequence means that a native RBS sequence is mutated, for example, by deletion, insertion or substitution of a base. Ribosomes bind to regions rich in purine bases (adenine and guanine) of 3 to 9 base length. Thus, the frequency of expression can be suppressed by reducing the content of these bases. For example, the modification of the RBS sequence can be a mutation that reduces the number of adenine and/or guanine in a region rich in purine bases of 3 to 9 base length as described above by deletion, substitution, or the like. Examples of the base to be substituted include adenine or guanine with thymine or cytosine. That is, examples of the modification include mutations substituting one or more purine bases with 1 to 7 thymine or cytosine bases in regions rich in purine bases of 3 to 9 base length as described above. For example, the modified RBS sequence may include substitutions, deletions, or insertions of 1 to 10 bases relative to the native RBS sequence. The modified RBS sequence may also include, for example, substitutions of 1 to 9 bases, 1 to 8 bases, 1 to 7 bases, 1 to 6 bases, 1 to 5 bases, 1 to 4 bases, 1 to 3 bases, or 1 to 2 bases relative to the native RBS sequence. The modified RBS sequence may also include, for example, a mutation substituting a with c at the 8th from the 5' end, or ga with tc at the 7th to 8th from the 5' end in the sequence of RBS1 represented by SEQ ID NO: 3, or a mutation corresponding thereto in other native RBS sequences. For corresponding mutations in other native RBS sequences, positions including the above mutations in RBS1 in the other native RBS sequences may be identified and modified to include similar mutations, for example, using conventional known methods such as sequence alignment methods.

A spacer having any sequence may or may not be present between the terminator sequence and the RBS sequence. The length of the spacer is not particularly limited as long as it can perform transcription control functions.

[Expression of Protein]

The expression cassette of the present invention is inserted into an expression vector to use for expression of a protein.

Expression vectors can be used either for self-replication in a host cell or for integration into a genomic DNA of a host cell. The type of expression vector can be appropriately selected, for example, from plasmid vectors, viral vectors, cosmid vectors, fosmid vectors, and artificial chromosomal vectors, according to the type of host cell.

As host cells, any of the prokaryotic cells and eukaryotic cells such as yeast cells, filamentous fungal cells, insect cells, animal cells, and plant cells can be suitably employed.

Examples of the host cells of prokaryotes such as bacteria include microorganisms belonging to the genera *Escherichia*, *Brevibacillus Serratia*, *Bacillus*, *Microbacterium*, *Brevibacterium*, *Corynebacterium*, and *Pseudomonas*. Preferred examples of prokaryotes include *E. coli*, *Bacillus subtilis*, *Pseudomonas*, *Corynebacterium*, and *Lactococcus*. It is preferable that the host cell is *Escherichia coli*.

Examples of microorganisms belonging to the genus *Escherichia* include *Escherichia coli* BL21 (Novagen), *Escherichia coli* BL21 (DE3) (Life Technologies), *Escherichia coli* BLR (DE3) (Merck Millipore), *Escherichia coli* DH1, *Escherichia coli* GI698, *Escherichia coli* HB101, *Escherichia coli* JM109, *Escherichia coli* K5 (ATCC 23506), *Escherichia coli* KY3276, *Escherichia coli* MC1000, *Escherichia coli* MG1655 (ATCC 47076), *Escherichia coli* No. 49, *Escherichia coli* Rosetta (DE3) (Novagen), *Escherichia coli* TB1, *Escherichia coli* Tuner (Novagen), *Escherichia coli* Tuner (DE3) (Novagen), *Escherichia coli* W1485, *Escherichia coli* W3110 (ATCC 27325), *Escherichia coli* XL1-Blue, and *Escherichia coli* XL2-Blue.

As methods for introducing the expression cassette into the host cell, any method for introducing DNA into the host cell can be used. Examples thereof include methods using calcium ions [Proc. Natl. Acad. Sci. USA, 69, 2110 (1972)], protoplast methods (Japanese Unexamined Patent Publication No. S63-248394), and methods described in Gene, 17, 107 (1982) and Molecular & General Genetics, 168, 111 (1979).

Transformation of microorganisms belonging to the genus *Brevibacillus* can be performed, for example, by the method of Takahashi et al. (J. Bacteriol., 1983, 156: 1130-1134), the method of Takagi et al. (Agric. Biol. Chem., 1989, 53: 3099-3100), or the method of Okamoto et al. (Biosci. Biotechnol. Biochem., 1997, 61: 202-203).

Examples of the vectors that introduce the expression cassette (hereinafter simply referred to as "vectors") include pBTrp2, pBTac1, pBTac2 (all commercially available from Boehringer Mannheim Corp.), pKK233-2 (manufactured by Pharmacia Corporation), pSE280 (manufactured by Invitrogen), pGEMEX-1 (manufactured by Promega Corporation), pQE-8 (manufactured by QIAGEN), pKYP10 (Japanese Unexamined Patent Publication No. S58-110600), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM B-400), Japanese Unexamined Patent Publication No. S60-221091], pGKA2 [prepared from *Escherichia coli* IGKA2 (FERM BP-6798), Japanese Unexamined Patent Publication No. S60-221091], pTerm2 (U.S. Pat. Nos. 4,686, 191, 4,939,094, 5,160,735), pSupex, pUB110, pTP5, pC194, pEG400 [J. Bacteriol., 172, 2392(1990)], pGEX (manufactured by Pharmacia Corporation), and pET System (manufactured by Novagen).

When *E. coli* is used as a host cell, examples of the suitable vector include pUC18, pBluescript II, pSupex, pET22b, and pCold.

Specific examples of the vectors suitable for microorganisms belonging to the genus *Brevibacillus* include those known as vectors for *Bacillus subtilis*, such as pUB110, pHY500 (Japanese Unexamined Patent Publication No. H2-31682), pNY700 (Japanese Unexamined Patent Publication No. H4-278091), pHY4831 (J. Bacteriol., 1987, 1239-1245), pNU200 (UDAKA JUZO, Nihon Nogei kagaku-kai shi (Journal of The Japan Society for Bioscience, Biotechnology, and Agrochemistry), 1987, 61: 669-676), pNU100 (Appl. Microbiol. Biotechnol., 1989, 30: 75-80), pNU211 (J. Biochem., 1992, 112: 488-491), pNU211R2L5 (Japanese Unexamined Patent Publication No. H7-170984), pNH301 (Appl. Environ. Microbiol., 1992, 58: 525-531), pNH326, pNH400 (J. Bacteriol., 1995, 177: 745-749), pHT210 (Japanese Unexamined Patent Publication No. H6-133782), pHT110R2L5 (Appl. Microbiol. Biotechnol., 1994, 42: 358-363), and pNCO2, a shuttle vector between *E. coli* and microorganisms belonging to the genus *Brevibacillus* (Japanese Unexamined Patent Publication No. 2002-238569).

Examples of the host cells of eukaryotes include yeast and filamentous fungi (such as mold).

Examples of the yeast include yeasts belonging to the genera *Saccharomyces, Schizosaccharomyces, Kluyveromyces, Trichosporon, Schwanniomyces, Pichia, Candida, Yarrowia*, and *Hansenula*.

When yeast is used as a host cell, it is preferable that expression vectors typically include an origin of replication (if amplification in the host cell is required), a selection marker for vector proliferation in *E. coli*, an inducible promoter and terminator for recombinant protein expression in yeast, and a selection marker for yeast.

If the expression vector is a non-integrating vector, it is preferable that the expression vectors further include an autonomous replication sequence (ARS). Inclusion of ARS can improve the stability of expression vectors in cells (Myers, A. M., et al. (1986) Gene 45: 299-310).

Examples of the vectors when yeast is used as a host cell include YEP13 (ATCC37115), YEp24 (ATCC37051), YCp50 (ATCC37419), YIp, pHS19, pHS15, pA0804, pHIL3Ol, pHIL-S1, pPIC9K, pPICZα, pGAPZα, and pPICZ B.

Specific examples of the promoters when yeast is used as a host cell include galactose-inducible gal 1 and gal 10 promoters; copper-inducible CUP 1 promoters; thiamine-inducible nmt1 promoters; and methanol-inducible AOX1, AOX2, DHAS, DAS, FDH, FMDH, MOX, ZZA1, PEX5-, PEX8-, and PEX14-promoters.

Methods for introducing expression vectors into yeast can be any method for introducing DNA into yeast, and examples thereof include electroporation methods (Methods Enzymol., 194, 182 (1990)), spheroplast methods (Proc. Natl. Acad. Sci., USA, 81, 4889 (1984)), lithium acetate methods (J. Bacteriol., 153, 163 (1983)), and methods described in Proc. Natl. Acad. Sci. USA, 75, 1929 (1978) or the like.

Examples of filamentous fungi include fungi belonging to the genera *Acremonium, Aspergillus, Ustilago, Trichoderma, Neurospora, Fusarium, Humicola, Penicillium, Myceliophtora, Botryts, Magnaporthe, Mucor, Metarhizium, Monascus, Rhizopus*, and *Rhizomucor*.

Specific examples of promoters when filamentous fungus is used as a host cell include salicylic acid-inducible PR1a promoters; cycloheximide-inducible Place promoters; and quinic acid-inducible Pqa-2 promoters.

The introduction of expression vectors into filamentous fungi can be accomplished using conventional known methods. Examples of such methods include a method of Cohen et al. (calcium chloride methods) [Proc. Natl. Acad. Sci. USA, 69: 2110 (1972)], protoplast method [Mol. Gen. Genet., 168: 111 (1979)], competent methods [J. Mol. Biol., 56: 209 (1971)], and electroporation methods.

The host cells into which expression cassettes of the present invention have been introduced are also referred to herein as "recombinant cells". Examples of the methods for introducing an expression cassette of the present invention into a host cell include a method of transforming an expression vector into which an expression cassette is introduced into a host cell, and a method of directly incorporating the expression vector or the expression cassette into a genomic DNA of the host cell. As the methods for transforming a host cell with an expression vector into which an expression cassette is introduced, any known methods can be used. Examples of such methods include a method for transforming a host cell with an expression vector using a plasmid. Recombinant *E. coli* can be produced by introducing an expression cassette into *E. coli* by the methods described above.

As the methods for incorporating the above expression vectors or expression cassettes into the genomic DNA of a host cell, any known methods can be used. Examples of such methods include λred methods employing recombinant mechanisms in the repair of double-strand breaks of λ phage, Red/ET homologous recombination methods, and transfer methods utilizing transposon activity using pUT-mini Tn5. Furthermore, an expression cassette can be incorporated into a genomic DNA of a host cell using "a gene transfer kit by transposon pUT mini-Tn5 kit" manufactured by Biomedal S.L. in accordance with the method described in the kit.

[Culture Method]

The protein encoded by the gene of an expression cassette according to the present invention are obtained by culturing and expressing a host cell (recombinant cell) into which the expression cassette was introduced in a culture medium. The method of culturing recombinant cells according to the present invention in a culture medium can be performed according to the method commonly used for culturing recombinant cells. In the case of culture for producing a protein of interest, recombinant cells may be cultured under conditions in which the protein of interest can be expressed.

Culture methods according to the present embodiments can include batch culture, semi-batch culture (fed-batch culture), and continuous culture.

When culture for growth is carried out by a fed-batch culture, the fed-batch substrate solution can contain, for example, one or more nutrients of the medium components. The feed of the fed-batch substrate solution may be performed in a continuous manner, discontinuous manner, or the like, according to the methods known in the art. There is no particular limitation on the amount of feed, and the feed may be performed by a combination of linear constant coefficient method, linear increment method, stepwise increment method, exponential feed method, or the like, using the mass of bacteria grown as an indicator. The mass of bacteria can be confirmed, for example, by dry weight of bacteria, wet weight of bacteria, or colony-forming units. By performing the feed, recombinant cells can be cultured at high densities.

There is no specific limitation on the type of medium used for culture. Either natural or synthetic medium may be used if the medium contains carbon sources, nitrogen sources, inorganic salts or the like which recombinant cells can assimilate, and recombinant cells can be efficiently cultured in the medium.

The carbon source may be any carbon source which the recombinant cells can assimilate, and examples thereof include glucose, fructose, sucrose, and molasses containing these, carbohydrates such as starch and starch hydrolysates, organic acids such as acetic acid and propionic acid, and alcohols such as ethanol and propanol.

Examples of the nitrogen source include ammonia, ammonium salts of inorganic or organic acids such as ammonium chloride, ammonium sulfate, ammonium acetate and ammonium phosphate, other nitrogen-containing compounds, as well as peptones, meat extracts, yeast extracts, corn steep liquors, casein hydrolysates, soybean meal and soybean meal hydrolysates, and various fermented bacteria and digestions thereof.

Examples of the inorganic salt include first potassium phosphate, second potassium phosphate, magnesium phosphate, magnesium sulfate, sodium chloride, ferrous sulfate, manganese sulfate, copper sulfate, and calcium carbonate.

The culture temperature is, for example, 15 to 40° C. When recombinant E. coli transformed with an expression cassette is used, it is preferable that the culturing step of E. coli includes a pH adjustment step. It is preferable that the pH of the culture solution during culture is maintained at 3.0 to 9.0. By adjusting the pH to a constant range of the lower limit of 6.0 or more, preferably 6.5 or more, even more preferably 7.0 or more, and the upper limit of 9.0 or less, preferably 8.5 or less, even more preferably 8.0 or less, the growth of recombinant cells can be promoted and the productivity of the protein of interest can be improved. The pH of the culture solution can be adjusted using inorganic acids, organic acids, alkali solutions, urea, calcium carbonate, ammonia, and the like.

[Induction of Expression]

Expression induction of this expression cassette is performed by activating transcription (a transcription of a nucleic acid encoding a protein of interest) by a promoter. Activation of the promoter can be performed according to the methods known in the art, depending on the type of promoter. Activation of the promoter when the expression cassette is introduced into E. coli may be performed, for example, by drug induction, temperature change induction, or starvation induction.

When a promoter activated by the presence of an inducing substance (expression inducer) is used, expression of the expression cassette can be induced by adding the inducing substance to the culture solution. The inducing substance may be selected from the group consisting of IPTG, arabinose, β-indoleacrylic acid, rhamnose, and xylose, and when the expression cassette is introduced into E. coli, it is preferable that the inducing substance is IPTG. Furthermore, for example, when a T7 promoter, tac and trc promoters, and lac and lacUV5 promoters are used, it is preferable that the inducing substance is IPTG; when an araBAD promoter is used, it is preferable that the inducing substance is arabinose; when a trp promoter is used, it is preferable that the inducing substance is β-indoleacrylic acid; when a rhaBAD promoter is used, it is preferable that the inducing substance is rhamnose; and when xylF and xylA promoters are used, it is preferable that the inducing substance is xylose. The inducing substance may be added to the culture solution at once or multiple times by divided portions or may be added to the culture solution by continuous feeds. The fed-batch substrate solution may contain an inducing substance to feed. The amount of the inducing substance to be added can be set depending on the type of inducing substance and promoter, but for example can range from 0.1 to 30 preferably from 0.5 to 20 μg, per gram of dry weight of recombinant cells.

When a promoter activated by starvation is used, protein expression can be induced by using a medium that does not contain a particular substance, by using a medium that reduces the concentration of the substance, or by reducing the concentration of the substance in the medium by consuming the substance. Examples of the substance to be subjected to starvation include tryptophan, phosphoric acid, and glucose. For example, when a trp promoter is used, tryptophan starvation is preferred; when a phoA promoter is used, phosphate starvation is preferred; and when a cstA promoter and a cstA-lacZ promoter are used, glucose starvation is preferred.

When a promoter activatable by an increase or decrease of temperature is used, expression of the protein can be induced by increasing or decreasing the temperature of the culture solution. For example, when a PR promoter or a PL promoter of λ phage activatable by temperature increase is used, the temperature of the culture solution at the time of growth ranges from 20 to 37° C. to suppress expression of the recombinant protein at the time of growth, and then the expression of the protein can be induced by increasing the temperature of the culture solution to 38 to 44° C. In order to mitigate the effect of heat shock proteins at this time, a more stable expression induction can be performed by setting the pH of the culture solution during growth to 6.5 to 7.5 and varying the pH of the culture solution from 4.5 to 6.5 at the time of initiation of expression induction of the protein as described in Japanese Unexamined Patent Publication No. H6-292563.

The timing of transition from the stage at which the proliferation of recombinant cells is performed to the stage at which expression of the present expression cassette is induced is not particularly limited and can be set as appropriate depending on the configuration of the culture system and the design of the production process. From the viewpoint of efficiently producing a protein of interest, it is preferable to initiate the induction of expression of the expression cassette when the proliferation of recombinant cells reaches the mid to late phases of the logarithmic growth phase.

The growth of recombinant cells begins with a delay or induction phase (a period of slow increase in the number of cells at the beginning of culture), followed by a logarithmic growth phase (a period of two-fold logarithmic increase in the number of cells per unit time) to a constant phase (a period in which there is no change in the net number of cells). The mid phase of the logarithmic growth phase refers to the period when the number of cells becomes intermediate between the number of cells in the delay phase and the number of cells in the constant phase, while the late phase of the logarithmic growth phase refers to the period from the mid to the constant phases. As specific examples of the period at which the induction of expression of the expression cassette is initiated, for example, when recombinant cells whose value of $OD_{600}$ at a constant phase is about 150 are used, the period is preferably a period at which the value of $OD_{600}$ reaches 30 to 110, more preferably 40 to 90, and still more preferably 50 to 80.

The time period to induce expression of the expression cassette may last until the production amount is reached a set amount, depending on the host and protein type used. The production rate varies depending on the culture conditions such as the temperature of the culture solution, thus it is not necessary to definitively determine the time period to induce protein expression. The time period to induce expression of the recombinant protein may be set according to the progress of protein separation and purification in the next step. It is also preferable in industrial production to set a time to induce expression of the expression cassette so as not to affect the growth of recombinant cells performed in parallel and transfer of the grown recombinant cells.

From the culture solution in which the expression of the expression cassette is induced, the protein of interest can be separated and purified by the methods described below. Other proteins expressed by this expression cassette can be separated and purified similarly, if desired.

[Isolation and Purification of Protein of Interest] Isolation and purification of the protein of interest can be carried out in the methods commonly employed. For example, if the protein of interest is expressed in a lysed state in cells, isolation and purification thereof can be performed, for example, by the following methods.

After completion of culture to express the protein of interest, recombinant cells are recovered by centrifugation, and the recombinant cells is disrupted to obtain a cell-free extract. The disruption of recombinant cells can be carried out, for example, by crushing the recombinant cells, after suspension in aqueous buffer, with an ultrasound crusher, french press, Manton-Gaulin homogenizer, DYNO-MILL, or the like, by treatment of the recombinant cells by addition of drug such as enzymes, or by treatment of recombinant cells by addition of organic solvents or the like. The protein of interest can be isolated and purified by the methods commonly used for isolation and purification of proteins from the supernatants obtained by centrifuging the cell-free extract, that is the methods such as solvent extraction method, a salt precipitation method with ammonium sulfate or the like, a desalination method, precipitation method with an organic solvent, an anion exchange chromatography method using a resin such as diethylaminoethyl (DEAE)-sepharose, DIAION HPA-75 (manufactured by Mitsubishi Chemical Corporation), a cation exchange chromatography method using a resin such as S-Sepharose FF (manufactured by Pharmacia Corporation), a hydrophobic chromatography method with resins such as butyl cephalose and phenyl cephalose, a gel filtration method using molecular filtration, an affinity chromatography method, chromatofocusing method, and an electrophoresis method such as isoelectric focusing, alone or in combination.

When the protein of interest is expressed as an insoluble in cells, the insoluble body of the protein of interest is recovered as a precipitation fraction by similarly recovering recombinant cells, crushing them, and centrifuging them. The insoluble body of the protein of interest recovered can be solubilized with a protein denaturing agent. After the manipulation, a purification standard for the protein of interest can be obtained by an isolation and purification method similar to that described above.

If the protein of interest is present extracellularly by lysis of recombinant cells, the protein of interest can be recovered from the culture supernatant. That is, culture supernatants can be obtained by treating the culture solution by methods such as centrifugation, and the protein of interest can be isolated and purified from the culture supernatant by using the isolation and purification method similar to that described above.

Even when the protein of interest is secreted extracellularly, the protein of interest can be recovered from the culture supernatant. That is, culture supernatants can be obtained by treating the culture solution by methods such as centrifugation, and the protein of interest can be isolated and purified from the culture supernatant by using the isolation and purification method similar to that described above.

EXAMPLES

Hereinafter, the present invention will be described in more detail based on Examples. However, the present invention is not limited to the following Examples.

Example 1

(1) Synthesis of Nucleic Acids Containing a Gene Encoding a Protein of Interest and a Gene Encoding a Protein that Suppresses Expression Level, and Construction of Expression Vector. As the protein of interest, a spider silk protein (SSP) having the amino acid sequence represented by SEQ ID NO: 4 (PRT799) was designed based on the nucleotide sequence and the amino acid sequence of fibroin (GenBank Accession No. P46804.1, GI: 1174415) from *Nephila clavipes*.

Nucleic acids encoding proteins having the amino acid sequence of SEQ ID NO: 4 designed were each synthesized. To the nucleic acid, an NdeI site was added at the 5' end and an EcoRI site was added at downstream of the termination codon. The nucleic acid was cloned into a cloning vector (pUC118). After the nucleic acid was excised with NdeI and EcoRI restriction enzymes, the T7 promoter-inducible expression vector VEC214-GEN923 of the protein expression vector pET-22b (+) (GSL Biotech LLC), a plasmid vector, was obtained. Hereinafter, the region containing the promoter, spider silk, and terminator of the expression vector VEC214-GEN923 is referred to as a "pro-SSP-ter cassette" (cassette 0).

As the protein that suppresses expression level, proteins having activity of bacteriolysing host *E. coli*, and DNA degradation enzymes, deoxyribonucleases (DNase) were considered.

As genes encoding the protein having activity of bacteriolysing host *E. coli*, λSRRz (SEQ ID NO: 8) consisting of the gene S encoding holin of Enterobacteria phage lambda (GeneID: 5740919 of GenBank, NCBI, SEQ ID NO: 5), the gene R encoding endolysin (GeneID: 2703480 of GenBank, NCBI, SEQ ID NO: 6), and the gene Rz encoding cell lysis protein (GeneID: 2703481 of GenBank, NCBI; SEQ ID NO: 7), which are a bacteriolytic enzyme group, was used. At upstream of the nucleotide sequence of λSRRz, DNA (RBS1) having a nucleotide sequence of SEQ ID NO: 1 containing an RBS region was synthesized. The modified ones having the nucleotide sequence of SEQ ID NO: 9 (RBS2), SEQ ID NO: 10 (RBS3), SEQ ID NO: 11 (RBS4), or SEQ ID NO: 12 (RBS5) instead of the RBS region were also synthesized. RBS2 is the sequence in which a is substituted with c at the 8th from the 5'end of RBS1, RBS3 is the sequence in which ga is substituted with tc at the 7th to 8th from the 5' end of RBS1, RBS4 is the sequence in which aagga is substituted with ctttc at the 4th to 8th from the 5' end of RB 51, and RBS5 is the sequence in which aagaagga is substituted with tgcgtttc at the 1st to 8th from the 5' end of RBS1.

Each λSRRz containing the RBS1, 2, 3, 4, or 5 region at upstream was cloned into pUC118 as described above. The λSRRz containing the RBS1, 2, 3, 4, or 5 region at upstream was amplified with PCR using PrimeSTAR Max DNA Polymerase (manufactured by TaKaRa Bio, Inc.). For amplification of the λSRRz containing the RBS1 region (AAGAAGGAt), oligonucleotides of SEQ ID NO: 13 and SEQ ID NO: 14 were used as primers.

The amplified DNA fragments were treated with DpnI and inserted directly downstream of the pro-SSP-ter cassette of the expression vector VEC214-GEN923 using In-Fusion™ HD Cloning Kit (manufactured by TaKaRa Bio, Inc.) in accordance with the attached manual.

The regions containing the above inserted "pro-SSP-ter cassette" are hereafter referred to as "pro-SSP-ter-RBS1-λSRRz cassette" (cassette 1), "pro-SSP-ter-RBS2-λSRRz cassette" (cassette 2), "pro-SSP-ter-RBS3-λSRRz cassette" (cassette 3), "pro-SSP-ter-RBS4-λSRRz cassette" (cassette 4), and "pro-SSP-ter-RBS5-λSRRz cassette" (cassette 5), respectively.

As the protein whose expression level is to be controlled, deoxyribonuclease (DNase), endonuclease I from bovine pancreas was used. The DNase I of SEQ ID NO: 15, encoding endonuclease I derived from the amino acid sequence of GenBank: M60606, was synthesized. The DNase I gene was inserted directly downstream of λSRRz in a similar manner as described above to generate expression vectors in which the pro-SSP-ter-RBS1-λSRRz-DNase cassette (cassette 1D) and the pro-SSP-ter-RBS2-λSRRz-DNase (cassette 2D) were inserted into VEC214-GEN923, respectively.

(2) Production of Protein Expressing Strain

E. coli BLR (DE3) was transformed with each expression vector produced in (1) above to obtain a transforming strain (hereinafter also referred to as a "plasmid transforming strain").

Each cassette produced above was introduced into pUTmini-Tn5 using a pUTmini-Tn5 Kit by Biomedal S.L. in accordance with the manual attached to the Kit, and incorporated into the genomic DNA of E. coli to acquire a transformant strain (hereinafter also referred to as a "genomic DNA-integrated expression strain"). Specifically, the genomic DNA-integrated expression strains were acquired as follows. Each cassette region produced above was inserted into a NotI site of pUTmini-Tn5 Km to create a plasmid. The S17-1 λPir transformed strain with the plasmid was then mixed with E. coli BLR (DE3) at 1:1 and cultured in LB and Km-containing plate medium. From strains exhibiting Km resistance and Ap sensitivity, genomic DNA-integrated expression strains having incorporated fragments containing pro-SSP-ter-RBS (1, 2, 3, 4, or 5)-λSRRz-DNase, NotI-treated genomic DNA with each cassette, were acquired.

(3) Expression of Protein

Protein expression was evaluated by culture in L-tubes. Shaking culture was performed at 37° C. using LB medium, and IPTG was added at OD600=0.6 to 0.8 to induce expression.

The bacteriolytic strength was evaluated by measuring the growth rate before induction and the turbidity of the culture solution at OD600 after induction. The expression status of spider silk protein SSP was confirmed by the Bcinchoninic acid protein quantitation method (BCA method). That is, each SSP was dissolved by adding DMSO to the extract of culture bacteria and reacting at 85° C. for 30 minutes with stirring at 1500 rpm. After dissolution, the solution was diluted appropriately, and BCA Reagent A was added in the required amount and the mixture was dispensed into Eppendorf tubes. BCA Reagent B was added to the dispensed Eppendorf tube and the mixed solution was allowed to stand and reacted at 37° C. for 30 minutes. After the end of the reaction, the expression level of SSP was confirmed by measuring the absorption intensity of each sample. The results are shown in Table 1. SSP expression was evaluated in two scales of + and ++ with the expression level of cassette No. 0 as ++. The bacteriolytic strength was evaluated in four scales of − to +++ with that of the cassette No. 0 where no bacteriolysis was observed as −.

TABLE 1

| Cassette No. | Cassette Type | Strain type | SSP Expression | Bacteriolytic Strength |
|---|---|---|---|---|
| 0 | pro-SSP-ter | Plasmid | ++ | − |
| 1 | pro-SSP-ter-RBS1-λSRRz | | + | +++ |
| 2 | pro-SSP-ter-RBS2-λSRRz | | ++ | ++ |
| 3 | pro-SSP-ter-RBS3-λSRRz | | ++ | ++ |
| 4 | pro-SSP-ter-RBS4-λSRRz | | ++ | ++ |
| 5 | pro-SSP-ter-RBS5-λSRRz | | ++ | + |
| 1D | pro-SSP-ter-RBS1-λSRRz-DNase | | + | +++ |
| 2D | pro-SSP-ter-RBS2-λSRRz-DNase | | ++ | ++ |
| 0 | pro-SSP-ter | Genomic DNA | ++ | − |
| 1 | pro-SSP-ter-RBS1-λSRRz | | + | +++ |
| 2 | pro-SSP-ter-RBS2-λSRRz | | ++ | ++ |
| 1D | pro-SSP-ter-RBS1-λSRRz-DNase | | + | +++ |
| 2D | pro-SSP-ter-RBS2-λSRRz-DNase | | ++ | ++ |

From Table 1, it was confirmed that genes downstream of the terminator were expressed even via the terminator. It was confirmed by the absence of lysed bacteria during culture that the expression level of any gene downstream of the terminator was lower than that of SSP gene. It was confirmed that when the expression level of genes downstream of the terminator is high (with excellent bacteriolytic effect), there is a tendency that the expression level of the protein of interest, SSP, is decreased. However, it was also confirmed that modification of the ribosome binding site can control the expression level of genes downstream of the terminator, thereby enabling to increase the expression level of SSP (Table 1).

Example 2

Since efficacy was found in L-tube culture, evaluation in batch culture (1 L Jar culture) was performed by the following methods. Strains produced in Example 1 were inoculated in 2 mL of LB medium and cultured for 15 hours. The culture solution was added in 100 mL of the seed culture medium (Table 2) such that OD600 was 0.05.

TABLE 2

| Seed Culture Medium | |
|---|---|
| Reagent | Concentration (g/L) |
| Glucose | 5.0 |
| $KH_2PO_4$ | 4.0 |
| $K_2HPO_4$ | 9.3 |
| Yeast Extract | 6.0 |

The seed culture solution was added to 500 ml of production medium (Table 3) such that OD600 was 0.05, and the culture was performed at the temperature of 36±0.5° C. and pH of 6.3 to 6.1 in a jar fermenter.

TABLE 3

Production medium

| Reagent | Concentration (g/L) |
|---|---|
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| ADEKA NOL LG-295S (defoamer) | 0.1 (mL/L) |

The culture solution was agitated under aeration such that the dissolved oxygen concentration in the culture solution was maintained at 30 to 40% of the dissolved oxygen saturation concentration. For these controls, mass flow controllers (MPC0005BBRN0100D0, manufactured by Azbil Corporation) were used.

Immediately after complete consumption of glucose in the medium, feed solution (445 g/l L of glucose, 9 g/L of Yeast Extract) was added at a rate of 1 mL/min. Turbidity (OD600) was confirmed to be 60 or more, and 1 M isopropyl-β-thiogalactopyranoside (IPTG) was added to the culture solution to a final concentration of 0.1 mM to induce protein expression.

The timing of the culture termination was at 20 hours (T20) post-induction. Quantitative evaluation of proteins in the bacteria was compared by BCA method. The weight of bacteria (dry bacteria weight (g)) and the number of bacteria were simultaneously measured in the culture solution to calculate yield per bacterium.

After IPTG addition, the culture solution was sampled, and the bacteria was recovered at each time elapsed. SDS-PAGE was performed using bacteria prepared from the culture solution before and after IPTG addition to confirm expression of the protein of interest by the emergence of a band of protein size of interest dependent on IPTG addition.

Figure 2:
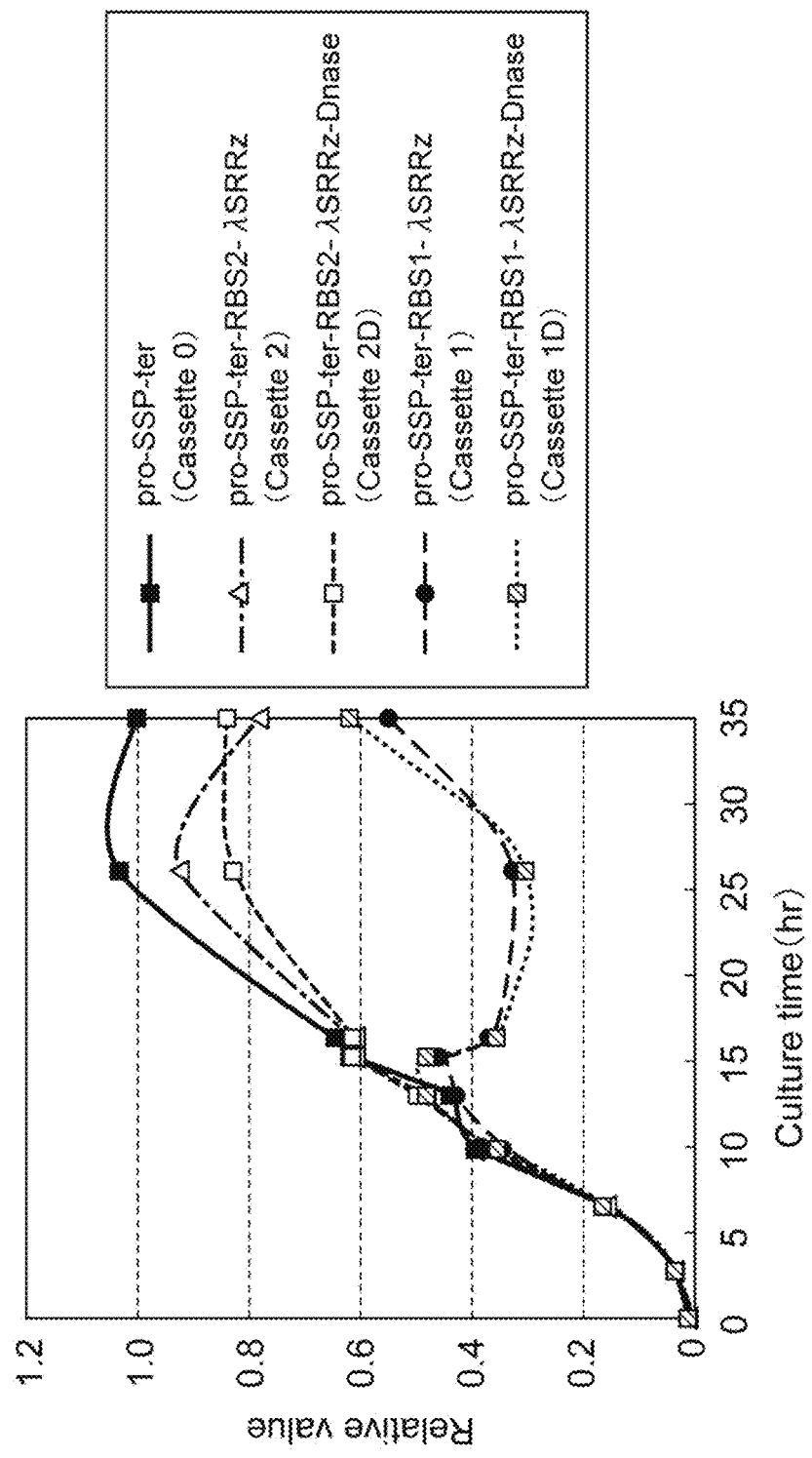
FIG. 2 is a graph showing the turbidity of culture solution in OD600 relative to culture time. The abscissa shows the culture time (hr) and the ordinate shows the relative value for the turbidity of the culture solution in OD600 at 35 hours from the start of the culture of cassette 0.

The chronological changes in protein expression using the genomic DNA-integrated expression strains in cassettes 0, 1, 2, 1D and 2D, respectively, are shown in FIG. 1, and the chronological changes in turbidity of the culture solution in OD600 is shown in FIG. 2. The values for each cassette in Table 4 are relative values based on cassette 0 at 20 hours post-induction (T20).

Cassette 1 genomic DNA-integrated expression strains and cassette 1D genomic DNA-integrated expression strains had lowered SSP expression level compared to strains that did not introduce the bacteriolytic enzyme group genes (FIG. 1). This is believed that due to the early strong expression of the bacteriolytic enzyme group genes in the cassette 1 genomic DNA-integrated expression strains and 1D genomic DNA-integrated expression strains, the bacteriolysis of the host had begun (FIG. 2). Cassette 2 genomic DNA-integrated expression strains in which the ribosome binding site was modified showed approximately equivalent SSP expression to the strains into which the bacteriolytic enzyme group genes were not introduced (FIG. 1). Furthermore, a reduction in turbidity was confirmed from the latter half of the culture (FIG. 2), thus it was confirmed that the host could be bacteriolysed at an appropriate time.

TABLE 4

| Cassette No. | Cassette Type | Strain type | Production amount (%) | Turbidity (%) |
|---|---|---|---|---|
| 0 | pro-SSP-ter | Genomic DNA | 100.0 | 100.0 |
| 1 | pro-SSP-ter-RBS1-λSRRz | | 73.2 | 55.1 |
| 2 | pro-SSP-ter-RBS2-λSRRz | | 100.3 | 78.2 |
| 1D | pro-SSP-ter-RBS1-λSRRz-DNase | | 64.4 | 61.9 |
| 2D | pro-SSP-ter-RBS2-λSRRz-DNase | | 105.1 | 84.1 |

Further Results using plasmid transforming strains of cassettes 3, 4 and 5, in each of which the ribosome binding site was modified, are shown in FIGS. 3 and 4. The values for each cassette in Table 5 are relative values based on cassette 0 at 20 hours post-induction (T20).

Any strain into which the bacteriolytic enzyme group genes were introduced showed approximately equivalent SSP expression to the strains into which the bacteriolytic enzyme group genes were not introduced (FIG. 3). Furthermore, a reduction in turbidity was confirmed from the latter half of culture (FIG. 4), thus it was confirmed that the bacteriolytic enzyme could bacteriolyse the host at an appropriate time.

TABLE 5

| Cassette No. | Cassette Type | Strain type | Production amount (%) | Turbidity (%) |
|---|---|---|---|---|
| 0 | pro-SSP-ter | Plasmid | 100.0 | 100.0 |
| 3 | pro-SSP-ter-RBS3-λSRRz | | 102.5 | 59.7 |
| 4 | pro-SSP-ter-RBS4-λSRRz | | 99.7 | 81.2 |
| 5 | pro-SSP-ter-RBS5-λSRRz | | 105.0 | 82.3 |

In the production of a protein using a host cell, the recombinant host cell needs to be treated by crushing or the like in order to recover the protein of interest, but such treatment can be alleviated if the bacteriolytic enzyme can act at an appropriate time as described above.

In addition, nucleic acids such as DNA are eluted from the crushed bacteria and increase the viscosity of the treatment solution to cause troubles in subsequent steps, but this can also be prevented by expressing DNase.

By way of comparison, after expressing a protein of interest to be produced, an attempt was made from another promoter to induce expression of another protein such as a bacteriolytic enzyme, but the host could not be properly bacteriolysed as described above.

The invention claimed is:

1. An expression cassette comprising, in a 5' to 3' direction of a sense strand, a promoter, and a first nucleic acid, a terminator and a second nucleic acid operably linked to the promoter, wherein the first nucleic acid and the second nucleic acid each comprises at least one gene, and the first nucleic acid and second nucleic acid are expressed under control of same said promoter, wherein an expression level of the gene comprised in the second nucleic acid is 20% or less of an expression level of the gene comprised in the first nucleic acid.

2. The expression cassette according to claim 1, further comprising a modified ribosome binding site (RBS) at downstream of the terminator and upstream of the second nucleic acid.

3. The expression cassette according to claim 1, wherein the first nucleic acid comprises a gene encoding a protein of interest.

4. The expression cassette according to claim 3, wherein the protein of interest is a protein selected from the group consisting of keratin, collagen, elastin, resilin, silkworm silk, and spider silk.

5. The expression cassette according to claim 1, wherein the second nucleic acid comprises a gene encoding a protein having a lysis activity on a host cell and/or a gene encoding a deoxyribonuclease.

6. The expression cassette according to claim 5, wherein the gene encoding a protein having a lysis activity on a host cell is selected from the group consisting of a lysozyme gene, a VanX gene, an S gene, an R gene, and an Rz gene.

7. The expression cassette according to claim 5, wherein the second nucleic acid contains the S gene, the R gene, and the Rz gene.

8. The expression cassette according to claim 5, wherein the gene encoding a deoxyribonuclease is a gene encoding DNase I.

9. The expression cassette according to claim 1, wherein the promoter is a T7 promoter.

10. The expression cassette according to claim 1, wherein the terminator is a T7 terminator.

11. A recombinant cell comprising the expression cassette according to claim 3 introduced there into.

12. A method for producing the recombinant cell according to claim 11, comprising introducing the expression cassette into a host cell using a plasmid.

13. A method for producing the recombinant cell according to claim 11, wherein the expression cassette is introduced into a genomic DNA of a host cell.

14. A method for producing a protein of interest, comprising culturing the recombinant cell according to claim 11 under conditions that enable the protein of interest to be expressed.

15. The method according to claim 14, comprising activating the promoter by induction by a drug, induction by a temperature change, or induction by starvation.

16. The method according to claim 15, wherein the induction by the drug is induction by IPTG.

* * * * *